US009474776B2

(12) United States Patent
Stamets

(10) Patent No.: US 9,474,776 B2
(45) Date of Patent: Oct. 25, 2016

(54) INTEGRATIVE FUNGAL SOLUTIONS FOR PROTECTING BEES

(71) Applicant: Paul Edward Stamets, Shelton, WA (US)

(72) Inventor: Paul Edward Stamets, Shelton, WA (US)

( * ) Notice: Subject to any disclaimer, the term of this patent is extended or adjusted under 35 U.S.C. 154(b) by 0 days.

(21) Appl. No.: 14/641,432

(22) Filed: Mar. 8, 2015

(65) Prior Publication Data
US 2015/0335689 A1 Nov. 26, 2015

Related U.S. Application Data

(60) Continuation-in-part of application No. 14/247,207, filed on Apr. 7, 2014, now abandoned, which is a continuation-in-part of application No. 13/986,978, filed on Jun. 20, 2013, which is a continuation-in-part of application No. 13/066,566, filed on Apr. 18, 2011, now Pat. No. 8,501,207, which is a division of application No. 12/288,535, filed on Oct. 20, 2008, now Pat. No. 7,951,389, which is a division of application No. 10/853,059, filed on May 24, 2004, now abandoned, which is a division of application No. 09/969,456, filed on Oct. 1, 2001, now Pat. No. 7,122,176, which is a continuation-in-part of application No. 09/678,141, filed on Oct. 4, 2000, now Pat. No. 6,660,290.

(60) Provisional application No. 62/074,023, filed on Nov. 2, 2014, provisional application No. 61/967,117, filed on Mar. 10, 2014.

(51) Int. Cl.
| A61K 36/07 | (2006.01) |
| A61K 36/074 | (2006.01) |
| A61K 45/06 | (2006.01) |
| A23L 1/30 | (2006.01) |
| A01K 51/00 | (2006.01) |
| A01K 47/06 | (2006.01) |
| A01N 65/00 | (2009.01) |
| A01M 1/20 | (2006.01) |

(52) U.S. Cl.
CPC ............... *A61K 36/07* (2013.01); *A01K 51/00* (2013.01); *A01N 65/00* (2013.01); *A23K 10/30* (2016.05); *A23K 20/00* (2016.05); *A23K 20/10* (2016.05); *A23K 20/111* (2016.05); *A23K 20/163* (2016.05); *A23K 50/90* (2016.05); *A23L 1/3018* (2013.01); *A61K 36/074* (2013.01); *A61K 45/06* (2013.01); *A23V 2002/00* (2013.01)

(58) Field of Classification Search
CPC .... A01K 51/00; A01K 53/00; A23K 1/1873; A23K 50/90; A61K 36/07; A61K 36/074; A01N 65/00
See application file for complete search history.

(56) References Cited

U.S. PATENT DOCUMENTS

| 6,183,742 B1 | 2/2001 | Kiczka | |
| 6,660,290 B1 | 12/2003 | Stamets | |
| 2002/0146394 A1* | 10/2002 | Stamets | ................. A01N 63/04 424/93.5 |
| 2012/0039976 A1* | 2/2012 | Stamets | ................. A01N 63/04 424/411 |

FOREIGN PATENT DOCUMENTS

| NZ | WO 2006/121350 B1 | 11/2006 |
| NZ | WO 2012/018266 A1 | 2/2012 |

* cited by examiner

*Primary Examiner* — Kortney L Klinkel
(74) *Attorney, Agent, or Firm* — William R. Hyde

(57) ABSTRACT

The present invention is based on a plurality of benefits from the extracts of mycelia of individual fungal species, and mixtures of species, to provide an armamentarium of defenses from multiple stressors in order to help bees survive a complex of symptoms collectively called colony collapse disorder (CCD). More particularly, the present invention utilizes specific concentrations of extracts from pure cultured mycelium from mushroom forming fungi to reduce harmful viruses in bees and to increase the longevity of bees.

14 Claims, 8 Drawing Sheets

INTEGRATIVE FUNGAL SOLUTIONS FOR PROTECTING BEES

CROSS-REFERENCE TO RELATED APPLICATIONS

This application claims the benefit of U.S. provisional patent application No. 62/074,023, filed Nov. 2, 2014, herein incorporated by reference in its entirety. This application is also a continuation-in-part of U.S. patent application Ser. No. 14/247,207, filed Apr. 7, 2014, which claims the benefit of U.S. provisional patent application No. 61/967,117, filed Mar. 10, 2014, both of which are hereby incorporated by reference in their entirety. This application is also a continuation-in-part of U.S. patent application Ser. No. 13/986,978, filed Jun. 20, 2013, which is a continuation-in-part of U.S. patent application Ser. No. 13/066,566, filed Apr. 18, 2011 (now issued as U.S. Pat. No. 8,501,207), which is a divisional of U.S. patent application Ser. No. 12/288,535, filed Oct. 20, 2008 (now issued as U.S. Pat. No. 7,951,389), which is a divisional of U.S. patent application Ser. No. 10/853,059, filed May 24, 2004, which is a divisional of U.S. patent application Ser. No. 09/969,456, filed Oct. 1, 2001 (now issued as U.S. Pat. No. 7,122,176), which is a continuation-in-part of U.S. patent application Ser. No. 09/678,141, filed Oct. 4, 2000 (now issued as U.S. Pat. No. 6,660,290), all of which are hereby incorporated by reference in their entirety.

STATEMENT REGARDING FEDERALLY SPONSORED RESEARCH OR DEVELOPMENT

Not Applicable.

THE NAMES OF PARTIES TO A JOINT RESEARCH AGREEMENT

Not Applicable.

INCORPORATION-BY-REFERENCE OF MATERIAL SUBMITTED ON A COMPACT DISC

Not Applicable.

BACKGROUND OF THE INVENTION

1. Field of the Invention

The present invention relates to compositions containing extracts of mycelia of fungal species, and their mixtures, to provide an armamentarium of defenses from multiple stressors in order to help bees survive a complex of symptoms collectively called colony collapse disorder (CCD). More particularly the present invention utilizes specific concentrations of consumable extracts from pure cultured mycelium from mushroom forming fungi to reduce harmful viruses in bees and to increase the longevity of bees.

2. Description of Related Art Including Information Disclosed Under 37 CFR 1.97 and 1.98

Approximately 100,000 species of insects, birds and mammals are involved in the pollination of flowering plants. This includes almost 20,000 known species of bees. The Food and Agriculture Organization of the United Nations estimates that of the slightly more than 100 crop species that provide 90 percent of food supplies for 146 countries, 71 are bee-pollinated (mainly by wild bees), and several others are pollinated by thrips, wasps, flies, beetles, moths and other insects. The annual monetary value of pollination services in global agriculture could be as high as $200 billion. *Protecting the Pollinators*, Food and Agriculture Organization of the United Nations. The co-evolution of plants and bees (*Apis* species) is fundamental to their mutual survival. The bees spread pollen and many plants produce rich nectar in return.

Approximately 4,000 bee species are native to North America. With the introduction of European (or "western") honey bees (*Apis mellifera*) to North America by colonists, commercial orchards and farms that would not normally be able to survive have thrived, although many New World crops and native flowering plants are primarily dependent upon native bee species for pollination. Asian agriculture is similarly dependent upon the Asian (or "eastern") honey bee (*Apis cerana*), although typically on a smaller and more regionalized scale (*A. mellifera* has also been introduced). Throughout agriculture the number of fruit, nut and vegetable crops benefitting from bee pollination is staggering, as are the number of flowering trees, shrubs and wildflowers. Indeed it is difficult to overstate the role of bees in the commercial production of food. The loss of bees we are experiencing now is unprecedented and a huge threat to food security worldwide. In some regions of China, for instance, the loss of bees has necessitated hand pollination to save crops, a dauntingly difficult task.

A honey bee hive is a warm, moist, densely populated environment inhabited by closely related individuals—the perfect setting for viruses, bacteria, fungi, protozoa and mites. Bees have successfully protected themselves for millions of years from such threats with unique colony-level and individual-level host defense systems and immune responses, but these defenses may be breaking down as the result of intense domestication of the European honey bee and multiple threats, including new anthropogenic stressors, resulting in a precipitous decline in the number of feral honey bees and native bees in areas including North America, Europe and China from 1972 to 2006, and the emergence of colony collapse disorder ("CCD") in honey bees in 2006.

The domestic honeybee industry is dependent upon queen breeding, the process of selection that brings about the lines to be propagated, and queen rearing, the process of producing and culling queen honey bees. The large majority of bee breeding in the United States is carried out by 10-15 large queen-producing companies, who exchange genetic information from about 500 breeder queens. Such limited genetic diversity may contribute to susceptibility to various diseases, pests or colony collapse disorder. Particularly damaging to the rearing of queens are viruses, especially the Black Queen Cell Virus and other viruses including the Deformed Wing Virus, the Israeli Acute Bee Paralysis Virus, and nearly two dozen others. More viruses are anticipated to be discovered that contribute to illness in bees, including queens, their brood, in workers, nurse bees and drones.

Colony losses and bee disappearances have occurred throughout the history of beekeeping ("apiculture"), including various honey bee syndromes in the 1880s, the 1900s through the 1920s, the 1960s and the 1990s, such as "disappearing disease," "spring dwindle," "fall dwindle," "autumn collapse" and "mystery disease." In 2006, some beekeepers began reporting unusually high losses of 30-90 percent of their hives. This disappearing bee affliction was renamed "colony collapse disorder" (CCD, sometimes referred to as spontaneous hive collapse or Mary Celeste syndrome in the UK). CCD may or may not be related to the prior colony loss syndromes; it may be a genuinely new disorder or a known disorder that previously only had a minor impact.

CCD is now approaching 30-40% with many beekeepers; with the 'factory farms,' where up to 84,000 beehives are kept in one location, CCD can claim more than 60%. This has raised the costs for almond tree pollination, for example, from $25-30 per bee colony per ½ to 1 acre of almond orchard for 3 weeks to more than $250. More than ⅓ of all the non-animal food Americans consume is dependent upon pollination from bees. Should this upward trend in bee colony losses continue, the economic and societal expenses could run into the hundreds of billions of dollars.

The loss of the services provided by bees has other far-reaching implications. For example, Neem trees, the source of thousands of popular health, beauty and insecticide products, are dependent upon pollination from bees, which are not adversely affected. Interestingly, Neem products that contain the active ingredient, azadirachtin, are useful for limiting or killing mites, including *Varroa* mites that transmit diseases to bees, and including mites that transmit diseases to other animals and plants. Should bees be lost, so too will this vast resource of health products and a natural insecticide.

The main symptoms of CCD are the disappearance of the worker class (resulting in very few or no adult "worker" bees in the hive), a live queen and few to no dead bees on the ground around the colony. Often there is still honey in the hive, immature capped brood bees are present (bees will not normally abandon a hive until the capped brood have all hatched) and the hive contains honey and bee pollen that was not immediately robbed by neighboring bees. The hive is also slow to be robbed by colony pests such as wax moths or small hive beetles. *Varroa* mites, a virus-transmitting parasite of honey bees, have frequently been found in hives hit by CCD. Collapsing colonies typically do not have enough bees to maintain colony brood and have workers that consist of younger adult bees; the progression of symptoms may be rapid or slow (up to two years). The colony may have ample food stores and be reluctant to eat food provided by the beekeeper. See, for example, Honey Bees and Colony Collapse Disorder, United States Department of Agriculture Agricultural Research Service (2013).

The reasons for increasing colony collapse are complex and appear to be the result of multiple factors. Suggested causes include increasing urbanization and loss of biodiversity, particularly loss of wildflower meadows and "weeds" that provided high quality bee forage, poor nutrition and malnutrition, immunodeficiencies, microbial pathogens including viruses, bacteria, fungi and protozoa, both lethal and sub-lethal exposure to insecticides, fungicides and herbicides, beekeeper applied miticides and antibiotics, parasitic mites (*Varroa destructor* and *V. jacobsoni* mites and *Acarapis woodi* tracheal mites), the fungi *Nosema ceranae* and *N. apis*, heavy metals, toxic pollutants, natural plant toxins, biting insects, selective breeding in apiculture and loss of genetic diversity, climate change, concentrations of hives, and increased environmental stresses from drought and cold snaps, and combinations of these factors. Another factor is the new nature of the bee business and changing beekeeping practices. In the USA, there are few or, in many regions, no feral bees and domesticated bee colonies are often trucked hundreds of miles from factory bee 'livestock' apiaries, conferring additional stress factors to colony health and facilitating wider spread of infections and parasites amongst bee populations.

Although the exact cause(s) and mechanisms of CCD remain to be elucidated, it appears the combination of stressors is of importance, particularly 1) microbial viral and fungal pathogens such as Israeli Acute Paralysis Virus ("IAPV"), the Black Queen Cell Virus ("BQCV") and Deformed Wing Virus ("DWV") and *Nosema* (a pathogenic fungi); 2) parasitic mites (particularly *Varroa* mites); 3) pesticides at lethal or sub-lethal doses, including neonicitinoid insecticides (such as clothianidin, thiamethoxam, and imidacloprid) and beekeeper-applied miticides ("BAM") and other environmental stressors; 4) the management stressors of beekeeping including increasing viral exchange from trucked bees (particularly in the midwinter almond pollination migration to California), and 5) honey bee diets including use of honey substitutes and exposure to pollen of low nutritional value as opposed to native diverse pollen and nectar of high nutritional value. Research suggests that honey bee diets, parasites, diseases and multiple pesticides interact to have stronger negative effects on managed honey bee colonies, while nutritional limitation and exposure to sublethal doses of pesticides, in particular, may alter susceptibility to or the severity of bee parasites and pathogens. Pettis et al., Crop Pollination Exposes Honey Bees to Pesticides Which Alters Their Susceptibility to the Gut Pathogen *Nosema ceranae*, PLOS ONE, Published: Jul. 24, 2013, DOI: 10.1371/journal.pone.0070182.

Honey Bee Host Defense and Immune System:

Colonies of bees may be infected by several species of parasites or diseases at any time, but the colony-level and individual-level immune systems generally deal with the infections (with the possible exception of parasitic *Varroa destructor* mites) provided that environmental conditions are favorable. In the case of colony collapse, that normally effective immune function is clearly faltering. After the introduction of the parasitic, non-native *Varroa destructor* mite in 1987 to the United States, and its prolific spread throughout apiary populations, bees today face unprecedented threats from these virus-vectoring arthropods—fighting the viruses they introduce with immune systems weakened from exposure to complex cocktails of xenobiotic toxins. This convergence of stressors is a formula for disaster and is evolutionarily unprecedented. Additional stressors are the loss of plant biodiversity as forests are cut, wood is removed, and monoculture factory farms flatten the native landscapes. Bees, both domesticated and wild, our greatest pollinators, are under assault from multiple vectors. Bee extinctions have already been reported from some regions of China and are expected to occur with increasing frequency throughout the world.

Honey bees have numerous physical, chemical and behavioral defenses at the local population, colony hive, cell and individual bee levels. The first line of colony and individual defense is to avoid allowing parasites to gain a foothold—bees spend large amounts of energy on cooperative "social immunity" behaviors including grooming their body surfaces (both self auto-grooming and allo-grooming of a nest mate), cooperative hygienic behavior to detect and remove diseased brood and corpses of adult bees from the hive, cleaning the inner surfaces of the nest cavity and sterilizing all surfaces with antimicrobial secretions in their saliva (such as glucose oxidase), and utilizing (sometimes called "stealing") components of the plant immune system by gathering the highly antimicrobial resins found at leaf buds and wounds, incorporating them into propolis and using the propolis to form an antimicrobial barrier around the colony, including heavy use at the entrance, coating inner surfaces of the cavity and face of the comb and sealing cracks and crevices.

Individual Systemic Immune Response:

Insects possess innate immunity, which is characterized by non-specific immune reactions against invading pathogens, while lacking the complex "adaptive" or "acquired" immunity such as formation of antibodies specific to new pathogens. The defense mechanism in insects consists of cellular and humoral immunity. In the cellular defense mechanism, plasmocytes and granulocytes are the major haemocytes that react to foreign invaders either by phagocytosis and/or encapsulation. A hallmark of the humoral reactions is the synthesis and secretion of anti-microbial peptides (AMPs) that accumulate in the hemolymph and directly lyse foreign microbial cells and inhibit activities of enzymes essential for pathogen replication. See Yoshiyama, Innate immune system in the honey bee, Honey Bee Research Group, National Institute of Livestock and Grassland Science. This "induced" response of antimicrobial peptides can last for weeks, and it appears these peptides can be passed to nestmates to confer resistance prior to infection. Oliver, Sick Bees—Part 3: The Bee Immune System, American Bee Journal, October 2010.

The bee antiviral response is based upon RNA interference (RNAi). RNAi "silences" the expression of genes between the transcription of the genetic code and its translation into functional proteins. MicroRNA (miRNA, small non-coding RNAs that function in networks of protein-coding genes and cell physiological processes via transcriptional and post-transcriptional regulation of gene expression) and small interfering RNA (siRNA, short double-stranded fragments) bind to specific messenger RNA (mRNA) molecules and increase or decrease their activity, for example protein production or defending cells against viral nucleotide sequences. The miRNAs are a well-conserved, evolutionarily ancient component of genetic regulation found in many eukaryotic organisms.

RNAi is initiated by the enzyme Dicer, which cleaves long double-stranded (dsRNA) molecules into short double stranded fragments of siRNAs. Each siRNA is unwound into two single-stranded ssRNAs, the passenger strand and the guide strand. The guide strand is incorporated into the RNA-induced silencing complex (RISC). After integration into the RISC, siRNAs base-pair to their target mRNA and cleave it, thereby preventing it from being used as a translation template. When the dsRNA is exogenous (for example, coming from infection by a virus), the RNA is imported directly into the cytoplasm and cleaved to short fragments by Dicer.

Bees possess more RNAi pathway components relative to flies and appear to more readily mount a systemic RNAi response than do flies. It follows that bees should be quite capable of battling viruses and arguably other pathogens through knockdowns based on double-stranded RNAs of pathogen-expressed genes (Evans/Spivak 2009). Notably, this form of response to viral attack provides a long-term memory similar to that resulting from the antibodies produced in mammals. Oliver, Sick Bees—Part 4: Immune Response to Viruses, American Bee Journal, November 2010.

Viruses, *Nosema* and Microbial Pathogens:

Bees are host to at least 18 viruses, nearly all being single-stranded RNA viruses. Some are "emerging" pathogens, such as Deformed Wing Virus and Acute Bee Paralysis Virus, which were once considered to be "economically irrelevant" (Genersch 2010) and then, with the arrival of *Varroa* as a vector, began to visibly devastate colonies. Oliver, Sick Bees—Part 4: Immune Response to Viruses, American Bee Journal, November 2010.

Viral diseases include Chronic Paralysis Virus (CPV), Acute Bee Paralysis Virus (ABPV), Israeli acute paralysis virus (IAPV), Kashmir Bee Virus (KBV), Black Queen Cell Virus (BQCV), Cloudy Wing Virus (CWV), Sacbrood Virus (SBV), Deformed Wing Virus (DWV), Kakugo Virus, Invertebrate Iridescent Virus type 6 (IIV-6), Lake Sinai Viruses (LSV1 and LSV2) and Tobacco Ringspot Virus (TRSV). Within these viruses are many subtypes whose virulence towards bees is currently being investigated. More pathogenic viruses will likely be discovered. The co-occurrence of more than one internalized virus further challenges the immunological health of bees. "I do not know of any effective antiviral treatment in the market to fight the spectrum of viruses known to occur in honey bees."—Dr. Walter "Steve Sheppard, Chair, Department of Entomology, Washington State University, Pullman, Wash. (personal communication). Hence, there is a need for advantageous remedies, which are non-toxic, yet active against more than one virus.

Bees are also vulnerable to pathogen host shifts. The tobacco ringspot virus can replicate and produce virions in *Apis mellifera* honeybees, resulting in infections throughout the entire body, including extensive infection of the nervous system and likely impacts on colony survival. TRSV was also found in the gastric cecum of *Varroa* mites, suggesting that *Varroa* mites may facilitate the spread of TRSV in bees while avoiding systemic invasion. Li et al., Systemic Spread and Propagation of a Plant-Pathogenic Virus in European Honeybees, *Apis mellifera*, mBio 5(1):e00898-13. doi: 10.1128/mBio.00898-13. The virus, first observed in infected tobacco, is spread through infected pollen of numerous plant species including soy and numerous crops, weeds and ornamentals.

*Nosema apis* is a microsporidium, recently reclassified as a fungus, which invades the intestinal tracts of adult bees and causes *Nosema* disease, also known as nosemosis. *Nosema* infection is also associated with Black Queen Cell Virus and Kashmir Bee Virus. *Nosema ceranae* is becoming an increasing problem on both the Asian honey bee *Apis cerana* and the western honey bee.

Some honey bee viruses (DWV and KBV) and the fungi *Nosema ceranae* are able to infect other species of bees and wasps, and possibly *Varroa* gut cells; honeybees are likely the source of the bumblebee pathogens. Fürst et al., Disease associations between honeybees and bumblebees as a threat to wild pollinators, *Nature*, Volume: 506, 364-366, (2014). This new bee-to-bee vector could be a tipping point, causing wide scale collapse of many native bee species, with consequences well beyond our control, or imagination. From a historical and biological perspective, this is an 'all hands on deck' moment. What evolution has provided us over millions of years can be lost in decades due to the human interventions whose incentives are short term in view—at the expense of the long term.

Bacterial diseases of bees include American foulbrood (AFB), caused by *Paenibacillus larvae*, and European foulbrood (EFB), caused by the bacterium *Melissococcus plutonius*. Fungal diseases include Chalkbrood, caused by *Ascosphaera apis*, and Stonebrood, a fungal disease caused by *Aspergillus fumigatus, Aspergillus flavus*, and *Aspergillus niger*. New, as yet unidentified, fungal pathogens are expected to co-occur or become a primary cause of bee diseases in the future as humans further alter the natural environment and cause unintended consequences from the use of transgenic crops, more broadly known as GMOs— genetically modified organisms. Such potential fungal pathogens include *Candida, Cryptococcus, Coccidiodes* and other yeast-like organisms. And yet, many of these so-called pathogens, especially, for instance, the pre-sporulating forms of entomopathogenic fungi, have properties that can confer benefits to insects, including bees, provided that their endogenous toxins are eliminated, reduced or altered so to not harm bees, thereby reducing the threat to bees by disease-causing, disease-bearing or disease-spreading organisms.

All honey bees are infected by more than one species of bacteria, including beneficial endosymbionts that offer protection against yeasts, chalkbrood and foulbrood. Apparently healthy bees may also be infected by more than one species of virus. The dynamics of bee-bacteria, bee-virus and virus-virus interactions are complex and poorly understood. Certain bee viruses may enhance the virulence of other viruses while some bee viruses may competitively suppress the replication of others. So too there are likely bacteria-to-bacteria, bacteriophage-to-bacteria, fungi-to-bacteria and fungi-to-virus interrelationships scientists have yet to discover. Many virulent bee viruses can exist in an "unapparent" infection—one can detect the presence of the virus in bees, but there are no noticeable negative effects due to the infection. An infection by a second virus or other stressor may cause a dormant virus to start replicating. A number of researchers have found that the mere action of a *Varroa* mite feeding upon a bee (which includes injection of immune suppressants by the mite) may induce or activate the replication of unapparent and normally non-pathological virus infections. Studies of immune responses have also shown that mites and viruses could alter transcript levels of immunity-related genes in their corresponding hosts. It is common for collapsing colonies to be simultaneously infected with three or four viruses, *Varroa* mites, *Nosema* (*ceranae* and especially *apis*), and trypanosomes. See Oliver, Sick Bees—Part 3: The Bee Immune System, American Bee Journal, October 2010.

*Crithidia bombi* is a trypanosomatid protozoan bee parasite known to have serious effects on bumblebees, particularly under starvation conditions. The related *Crithidia mellificae* may be contributing to mortality in the honey bee. Ravoet et al., Comprehensive Bee Pathogen Screening in Belgium Reveals *Crithidia mellificae* as a New Contributory Factor to Winter Mortality (2013), *PLoS ONE* 8(8): e72443.

*Varroa* Mites and Other Parasites:

*Varroa destructor* and *Varroa jacobsoni* are parasitic mites that feed on the bodily fluids of bee adults, pupae and larvae. *Acarapis woodi* is a tracheal mite that infests the airways of the honey bee. The Asian parasitic brood mites *Tropilaelaps clareae* and *T. mercedesae* are considered serious potential threats to honeybees, although they have not been found in the United States or Canada to date.

The Asian honey bee *Apis cerana* is the natural host to the *Varroa jacobsoni* mite and the parasite *Nosema ceranae*. Having co-evolved with these parasites, *A. cerana* exhibits more careful grooming than *A. mellifera*, and thus has a more effective defense mechanism against *Varroa* and *Nosema*, which are becoming increasingly serious pests of the western honey bee.

*Varroa* mites breaching bees' hygienic, mechanical and physiological barriers to invasion have increasingly acted as a vector for viruses as well as causing major stress to bees. Widespread colony losses have only been reported from countries is which *Varroa* is a problem (Neumann 2010). Colonies without mites may be virus free (Highfield 2009), but up to 100% of colonies with *Varroa* may be infected by one or more viruses, even if there are no apparent symptoms (Tentcheva 2004). Oliver, Sick Bees—Part 1, American Bee Journal, August 2010.

*Varroa* mites have been found to be far more susceptible to acids than are honey bees. Organic acids such as oxalic acid, formic acid and lactic acid can be used as "natural miticides" or mite treatments in the hive, as they are all naturally found in honey. Oxalic acid is typically mixed with distilled water to prevent the formation of salts, resulting in an acidic solution with pH often times <1. That the bees can tolerate such a low pH while mites cannot is significant. The oxalic acid will capture calcium and other minerals from the exoskeleton of the mites to form oxalates. When direct contact of oxalic or formic acid with the chitinous like exoskeleton of the mites pulls out calcium, the exoskeleton is weakened, thus making the mites susceptible to other stressors, including but not limited to infection or toxin exposure from entomopathogenic fungi.

Besides known colony insect pests, such as the greater and lesser wax moths and the small hive beetle, the phorid fly, previously known to parasitize bumblebees, may be emerging as a threat to honey bees. Core et al., A New Threat to Honey Bees, the Parasitic Phorid Fly *Apocephalus borealis* (2012), *PLoS ONE* 7(1): e29639. doi:10.1371/journal.pone.0029639; Ravoet, supra.

Pesticides:

Pesticides cause multiple forms of stress to bees. Agricultural spraying may affect honey bees and large-scale spraying programs for mosquitoes, gypsy moths, spruce worms and other insect pests may cause direct or indirect bee kills including native bumblebees and solitary bees. There is also a shift in the types of pesticides applied—many, such as neonicitinoids, are less toxic to vertebrates and the necessity of repeated application is reduced, but they act systemically and are absorbed and distributed throughout the plant upon seed or soil treatment, including distribution to the pollen and nectar.

Sub-lethal pesticide exposure, including exposure to cholinergic neonicitinoid insecticides (nicotinic receptor agonists) and/or cholinergic organophosphate miticides (acetylcholinesterase inhibitors), has been found to alter bee activity, development, oviposition, behavior, offspring sex ratios, flight and mobility, navigation and orientation ability, feeding behavior, learning, memory and immune function, population dynamics and increase susceptibility to and mortality from diseases, including *Nosema*. See, for example, Pettis, Crop Pollination Exposes Honey Bees to Pesticides Which Alters Their Susceptibility to the Gut Pathogen *Nosema ceranae*, supra at 1. Fungicides and miticides used by beekeepers can have a pronounced ability on bees' ability to withstand parasite infection. Pettis, supra at 4. Often bees are exposed to a variety of pesticides, which may have interactive effects. See, for example, Di Prisco et al., Neonicitinoid clothianidin adversely affects insect immunity and promotes replication of a viral pathogen in honey bees, PNAS vol. 110, no. 46, Nov. 12, 2013, 18466-18471; Pettis et al., Crop Pollination Exposes Honey Bees to Pesticides Which Alters Their Susceptibility to the Gut Pathogen *Nosema ceranae, PLoS ONE* (2013); Palmer et al., Cholinergic pesticides cause mushroom body neuronal inactivation in honeybees, *Nature Communications,* 4:1634, (2013); Williamson et al., Exposure to multiple cholinergic pesticides impairs olfactory learning and memory in honeybees, *The Journal of Experimental Biology* 216, 1799-1807 (2013); Derecka et al., Transient Exposure to Low Levels of Insecticide Affects Metabolic Networks of Honeybee Larvae, *PLoS ONE* 8(7), e68191 (2013), doi:10.1371/journal.pone.0068191.

Exposure to fungicides also kills or reduces the beneficial fungi found on pollen—the result likely being a higher incidence of disease in honeybees, including *Nosema* infections and chalkbrood (ironically, fungal diseases).

The bee genome has relatively few genes that are related to detoxification compared to solitary insects such as flies and mosquitoes. Some of the most marked differences between bees and other insects occur in three superfamilies encoding xenobiotic detoxifying enzymes. Whereas most other insect genomes contain 80 or more cytochrome P450 (CYP) genes, *A. mellifera* has only 46 cytochrome P450 genes, whilst humans host about 60 CYP genes. Honey bees have only about half as many glutathione-S-transferases (GSTs) and carboxyl/cholinesterases (CCEs), compared to most insect genomes. This includes 10-fold or greater shortfalls in the Delta and Epsilon GSTs and CYP4 P450s, members of which clades have been linked to insecticide resistance in other species. Claudianos et al., A deficit of detoxification enzymes: pesticide sensitivity and environmental response in the honeybee, *Insect Molecular Biology*, 15(5), 615-636 (2006).

Whereas bees evolved to deal with plant phytochemicals and natural toxins, they now must additionally metabolize and detoxify anthropogenic insecticides, miticides, herbicides, fungicides and environmental pollutants, an unprecedented evolutionary challenge.

Management Stressors of Beekeeping:

Use of honey or pollen substitutes (such as sugar syrup; high fructose corn syrup; bee candy; "grease patties" containing grease, sugar and optionally salt or essential oils; or "pollen patties" containing soy, yeast and nonfat dry milk, which may have added pollen, possibly from areas contaminated with pesticides) may be a contributing factor to declining bee populations and CCD for several reasons. Malnutrition is likely a major factor in declining bee populations. Synthesized bee diets simply do not provide the nutritional value obtained by bees from a mixture of quality pollens. Although quality proteins, carbohydrates and vitamins can be provided to honey bees in the lab, we still cannot keep them alive more than two months in confinement on our best diets; they typically live, on average, about 30 days in captivity. Garvey, About Bee Nutrition . . . . , Posts Tagged: from the UC Apiaries newsletter—The California Backyard Orchard.

Honey contains several substances that activate nutrient sensing, metabolic, detoxification and immune processes in the European honey bee *Apis mellifera*, plus other chemicals useful to honey bee health. The enzymes are found on the pollen walls of flowers and enter the honey by sticking to the bees' legs. Ingestion of tree resins, balsams and tree saps via incorporation into propolis or bee glue is also known to reduce bee susceptibility to both insecticides and microbial pathogens and up-regulate the transcription of the detoxification genes. Honey substitutes or pollen patties, which don't contain these chemicals, may therefore contribute to colony collapse disorder. See Mao, Wenfru, Schuler, Mary A. and Berenbaum, May R., Honey constituents up-regulate detoxification and immunity genes in the western honey bee *Apis mellifera*, *Proceedings of the National Academy of Sciences of the United States*, 110(22), 8842-8846 (2013). Mao et al. found that constituents in honey derived from pollen and tree exudates, including p-coumaric acid (=4-hydroxycinnamic acid), pinocembrin, pinobanksin and pinobanksin 5-methyl ether, are strong inducers of cytochrome P450 genes detoxification genes via a number of CYP6 and CYP9 family members. Massively parallel RNA sequencing and RNA-seq analysis revealed that p-coumaric acid specifically up-regulates all classes of detoxification genes as well as select genes for antimicrobial peptides required for defense against pesticides and pathogens.

Those species of honey bees that nest in tree cavities use propolis to seal cracks in the hive, as do bees in domestic hives, although feral honey bees coat the entire inner surface of their nesting cavity, whereas domesticated honey bees lay down comparatively little resin in beekeeping hives. The coating of propolis has been demonstrated to inhibit AFB (Antúnez 2008), fungi, and wax moth; Spivak has demonstrated that propolis from some regions is effective against *Varroa*, and is investigating its effect on viruses. Of great interest is the finding (Simone 2009) that the abundance of propolis appears to decrease the necessary investment in immune function of bees—thus, the bee colony, by self-medicating with antimicrobial chemicals from plants, incurs less of a metabolic cost in fighting pathogens. Oliver, Sick Bees—Part 3: The Bee Immune System, American Bee Journal, October 2010.

Bears, Mushrooms and Bees:

The inventor noticed, on one of his many forays in the old growth forests of the Olympic Peninsula, Washington State, a conifer tree scratched by a bear (a photograph appears in the book he authored, *Mycelium Running: How Mushrooms Can Help Save the World*, 2005, pg. 70, FIG. 75. Ten Speed Press, Berkeley). The research literature on the inter-relationships between bears and mushrooms stated that *Fomitopsis* species, brown rotting polypore wood conks, including the frequently seen *Fomitopsis pinicola* and the rarely seen *Fomitopsis officinalis*, were the most common fungal species to grow after bear scratchings in conifer forests of the Pacific Northwest and elsewhere. Forest scientists showed that when bears scratch a living tree, they leave an open wound, and the *Fomitopsis* species opportunistically gain an entry site for infection. After a scratching, sugar-rich resin often beads out as droplets, attractive to bears and bees. Indeed, when the author returned a few years later to the same bear-scratched tree deep in the old growth forests along the south fork of the Hoh River, *Fomitopsis pinicola* mushrooms were fruiting from the now-fallen tree.

"On young conifers, particularly Douglas-fir trees, bears will rip strips of bark off with their teeth to reach insects or the sweet-tasting sap found inside. The bear's teeth leave long vertical grooves in the sapwood and large strips of bark are found around the bases of trees they peel. These marks are typically made from April to July, but the results may be seen all year. This foraging activity is common in tree plantations where large stands of trees are similarly aged and of a single species." Link, Living with Wildlife: Black Bears, Washington State Dept. of Fish and Wildlife.

For this reason, a bounty was placed upon bears by forest stakeholders since the bears were thought to reduce the profitability of forests for timber. Tens of thousands of bears were killed by hunters hired by the timber companies. In the 1990s, it was discovered that bears actually benefit the forests by bring sea minerals, particularly phosphorus and nitrogen, due to their foraging for salmon and trout in the rivers adjacent to the forests. One reason the lowland old growth forests are so much larger than old growth forests several thousand feet up in elevation, above the limit of the migrating fish, is that bears brought the carcasses of fish onto shore, benefitting the adjacent trees with phosphorus and other minerals that influence tree growth. Humans are particularly adept at making decisions contrary to their long-term best interests due to a fundamental misunderstanding about the interconnectedness of nature.

In Stamets, *Growing Gourmet and Medicinal Mushrooms*, 1993, p. 42-43, the current inventor stated "For 6 weeks one summer our bees attacked a King Stropharia bed, exposing the mycelium to the air, and suckled the sugar-rich cytoplasm from the wounds. A continuous convoy of bees could be traced, from morning to evening, from our beehives to the mushroom patch, until the bed of King Stropharia literally collapsed. When a report of this phenomenon was published in Harrowsmith Magazine (Ingle, 1988), bee keepers across North America wrote me to explain that they had been long mystified by bees' attraction to sawdust piles." Although it may not have been clear to one of ordinary skill in the art if the bees were attracted to the mycelium, the lignin within the sawdust or wood resins within the sawdust, the inventor concluded "Now it is clear the bees were seeking the underlying sweet mushroom mycelium."

An urgent solution is needed to the problems of declining bee health and colony collapse disorder.

BRIEF SUMMARY OF THE INVENTION

The present inventor sees the intersection and interplay of several mycological methods and compositions as a possible integrated solution to CCD. Each one of these elements may be sufficient to cause an effect leading to preventing or reducing CCD. As an integrated platform of partial solutions, the totality of these methods will achieve a synergistic benefit. More particularly, this invention focuses on the antiviral and longevity enhancing effects from extracts from pure cultured mycelium, diluted to within specific ranges, which proffer benefits to bees.

The basis of these compositions and methods include the extracellular exudates and extracts made therefrom, of the pure cultured mycelium, prior to fruitbody formation, in the mushroom species of the Agaricales, Polyporales and Hymenochaetales in combination or independently. Preconidial mycelium and extracts of the preconidial mycelium of entomopathogenic fungi may optionally be used to control mites and other bee and hive parasites. Mixtures of these extracts and bee products such as bee food or bee treatment sprays offer multiple solutions to help prevent CCD or help bees overcome CCD. Sustainable solutions to problems plaguing bees will be derived from promoting their natural defenses through habitat enhancement via beneficial fungi, such as introducing mushroom forming fungi that have antiviral properties to wood, causing rot, and ultimately moist nesting cavities that can be helpful to bees.

The inventor has isolated various strains of mushroom fungi, including *Pleurotus ostreatus, Trametes versicolor*, and *Psilocybe azurescens* that have demonstrated superior abilities to "bioremediate" or "mycoremediate" various toxins including oil, pesticides and nerve gases such as Sarin, Soman and VX (dimethylmethylphosphonate), working with Battelle Laboratories, a public report of which was published in Jane's Defence Weekly. (Fungi could combat chemical weapons, *Jane's Defence Weekly*, 1999. 32(7):37.)

The inventor has also isolated various strains of fungi, including *Fomitopsis officinalis, Fomitopsis pinicola, Ganoderma applanatum, Ganoderma annularis, Ganoderma lucidum, Ganoderma resinaceum, Inonotus obliquus, Irpex lacteus, Phellinus linteus, Piptoporus betulinus, Pleurotus ostreatus, Polyporus umbellatus, Schizophyllum commune*, and *Trametes versicolor* that have demonstrated superior antiviral, antibacterial, antifungal and antiprotozoal properties.

Without being bound to any theory, the inventor would hypothesize that these mushroom species are rich in compounds that up-regulate genes for detoxification and defense against pollutants, pesticides and pathogens in animals, including humans and bees. By repeatedly culturing and expanding non-sporulating sectors of entomopathogenic fungi, the inventor also discovered that such "pre-sporulating" or "preconidial" mycelium and extracts of preconidial mycelium emit odors and fragrances (ranging from *Metarhizium anisopliae* and *Aspergillus flavus* "butterscotch" to *Beauveria bassiana* "vanilla cola" and "hard Christmas candy") and tastes are attractive to animals including humans and both non-social and social insects, which offer advantages in control of pests such as *Varroa* mites.

The inventor now hypothesizes that the *Fomitopsis* colonization of the wood from bear foraging and the entry wound site (see above) would lead to the production of enzymes (laccases, lignin peroxidases, cellulases), ergosterols and other sterols, mycoflavonoids and especially arrays of nutritious complex polysaccharides that would not only soften the wood, provide water, nutrition, and emit fragrances, all of which would attract bees, while the extracellular exudates being secreted by the mycelium would be rich in p-coumaric acids and coumarins and the glycosides of unsubstituted and substituted benzoic, cinnamic and coumaric acids, all stimulating the up-regulation of innate cytochrome p450 genes and enzymes and also providing antiviral and antibacterial agents, all expressed during the decomposition of the infected tree. A complex fungal tree nectar is exuded, one that provides physiological benefits and boosts the innate immunity of bees via numerous pathways as the trees decompose. In some instances, bees nest within these logs or in the ground beneath them, benefitting from long-term contact. The bees can then incorporate these beneficial agents into their honey, propolis and combs so to as to protect the brood, the queen and ultimately the colony.

The inventor also hypothesizes that combinations of the fungal species including but not limited to their resident phenols above and below will have additive or even synergistic consequences, including regulation and up-regulation of nutrient-sensing, metabolic, detoxification, immunity and antimicrobial peptide genes and systems. This invention speaks directly to the link between the contact bees have with fungi that are beneficial, not only nutritionally, but especially in activating the cytochrome P450 pathways for deactivating and metabolizing xenobiotic and anthropogenic toxins.

The current invention provides a plurality of partial solutions to provide scientists, farmers, biotechnologists, policy makers and thought leaders with biological tools of practical and scalable remedies before ecological collapse forces us to ever-limiting options as biodiversity plummets. The combinations of these partial solutions cumulatively and synergistically provide that which is necessary for bees to overcome CCD.

Extracts of *Fomitopsis pinicola, Fomes fomentarius, Inonotus obliquus Ganoderma resinaceum* (*Ganoderma lucidum* var. *resinaceum*) and *Schizophyllum commune* have now been found to be effective in reducing the viral burden of honey bees and extending the life or worker bees. "As an entomologist with 39 years of experience studying bees, I am unaware of any reports of materials that extend the life of worker bees more than this."—Dr. Walter "Steve Sheppard, Chair, Department of Entomology, Washington State University, Pullman, Wash. (personal communication). The inventor now anticipates, as a consequence of this invention, that other woodland polypore mushrooms, for instance the birch polypore, *Piptoporus betulinus*, and numerous other woodland species will have greater and lesser antiviral and longevity enhancing effects on bee health when the extracts of the pure cultured mycelium are grown and diluted to within an optimal range, and presented as food, in the feed water, into honey, pollen patties, propolis, or even incorporated into the wood frames used to construct bee hives or incorporated into sticky strips applied to bee hives. The predominant viral species of concern are Deformed Wing Virus, Sacbrood virus, Israeli Acute Paralysis Virus and the Black Queen Cell Virus, each one of which may exacerbate the activity of other viruses, and pathogens, as immunity fails from the deleterious cumulative effect from these and other multiple stressors.

As Albert Einstein noted, "We cannot solve our problems with the same thinking we used when we created them." This patent follows this philosophy by offering a complex platform of synergistic solutions addressing a multiplicity of problems, which ultimately help bees overcome colony collapse disorder.

DETAILED DESCRIPTION OF THE INVENTION

Figure 1:
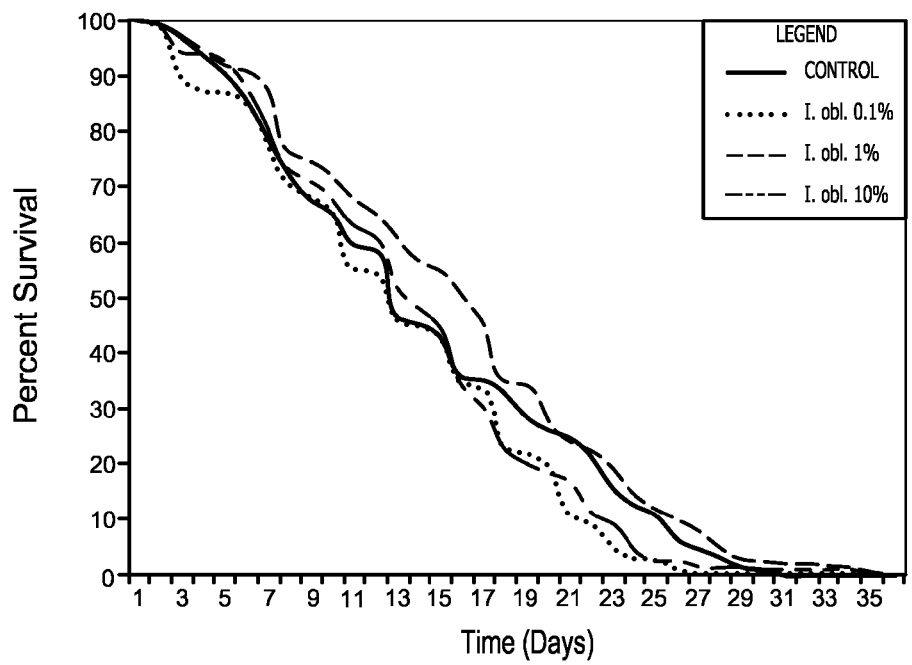
FIG. 1 is a line graph showing percent survival of bees over time when given extracts of the mycelium of *Inonotus obliquus* (0.1%, 1% and 10%) with sugar water as compared to a control population fed sugar water only.

Bees are increasingly dealing with new anthropogenic stressors. Over hundreds of millions of years fungi have evolved to fight viruses, bacteria and other fungi; have evolved to infect parasites, including insects; have evolved enzymes to break down toxins; and have evolved substances to up-regulate such processes. This means they offer a potential nutraceutical treasure trove of compounds useful for protecting bees and other pollinators from such threats, including a plurality of antiviral, antibacterial, antifungal and antiprotozoal compounds and compounds useful for up-regulating the digestive, detoxification and immune systems of bees.

Without being held to any one theory, the inventor hypothesizes that the fungal mycelium extracts specifically modulate, induce and increase the expression of detoxification and xenobiotic metabolizing genes, specifically to up-regulate all classes of detoxification genes, increase midgut metabolism of pesticides, function as a nutraceutical regulating immune and detoxification processes, up-regulate immune, metabolic and nutrient pathways (lipid and glucose-metabolizing pathways) and up-regulate genes encoding antimicrobial peptides. Moreover, select fungal species support the microbiome of beneficial microorganisms in the digestion systems of bees, and their compatibility is an important species-to-species bridge, matching beneficial wood rotting fungi to the beneficial microbes resident in the hindgut of bees. The extracts of the present invention are expected to be prebiotics for the natural microbiome within the bee's digestive organs as well as to confer antiviral benefits, all of which contribute to extending longevity of bees and their colonies, and their collective functionality. Another embodiment of this invention is to ferment the mycelium of medicinal mushrooms with *Bifidobacterium bifidum, Lactobacillus plantarum, Lactobacillus acidophilus, Lactobacillus sakei, Leuconostoc lactis, Streptococcus thermophiles* and bacteriophages to make consumable and environmentally applicable compositions beneficial to the microbiome of bees, animals (people).

Since bees are under assault from multiple pathogens— mites, viruses, microsporidia, protozoa, phorid flies and exposure to airborne pollutants—finding a robust broad-based platform of protection to help bolster the host immune defense of bees is of paramount importance. For example, developing methods for creating compositions using the extracellular exudates of the mycelium of select species of fungi, including but not restricted to *Stropharia rugoso-annulata* and other members of the Strophariaceae, *Fomitopsis pinicola* and other members of the Fomitopsidaceae and *Metarhizium anisopliae* and other members of the Clavicipitaceae, can help prevent colony collapse disorder.

Many other species of basidiomycetes and ascomycetes are also expected to confer similar benefits in the course of research into the benefits of bee-beneficial exudates secreted by the laboratory grown, pure cultured mycelium.

With regard to fungal extracts, mycelial extracts are preferred to "mushroom extracts" because the hyphae produce extracellular exudates that are rich in accessible water, oils, polysaccharides, amino acids, B vitamins, coumarins, p-coumaric acids, phenols and polyphenols, as well as ergosterols, enzymes, acids, including fatty acids, antibacterials and antivirals. The individual hyphal threads of the mycelium emits complex scents that volatilize into the air whereas the mushrooms tend to be nutritionally dense but do not have the extensive, exposed cellular surface area as the same mass of mycelium. The mushroom fruitbody is composed of cellularly compacted hyphae, laminated together, so only a small fraction of the mycelial mass in the fruitbody is exposed to the atmosphere. Hence the mushroom fruitbodies lack the fragrance attributes of the mycelium from which they form. Since these extracellular exudates can readily dissolve into solution, these exudates can be more usefully incorporated into amendments, such as pollen patties, sugar solutions or water, bee sprays or foliar plant sprays, and are better attractants to bees and other insects than the mushroom fruitbodies. This is not currently obvious to those skilled in the arts of mycology or entomology, whose focus has been more on the fruitbodies and spores from fruitbodies, rather than the mycelium.

Although bees may seek the sugar rich droplets exuding from the mycelium rotting wood, the extracts at 100%—what the bees would be sipping—are far too potent and toxic in most species in their natural form to be of benefit. Even at 10%, a majority the tested extracts were toxic. Hence, if bees were to sip these droplets in nature, they would likely sicken, prematurely die and not reap benefits. The inventor and his team discovered, that when the laboratory pure culture extracts were highly diluted, to 10%, some toxicity remained but when further diluted to 1% or 0.1% or less, longevity substantially increased, especially in midlife, when the workers are at the peak of their vigor and most productive in their foraging and pollen acquisition. Similarly, when the extracts were diluted, antiviral benefits were seen at the same time longevity increased in several fungal species tested. This is especially important as the reduction of the pathogen payload has an overall net benefit to the quality of the hive's overall health and performance. By combining extracts optimized for antiviral activity with extracts optimized for longevity, greater benefits than either are anticipated. Combined with longevity benefits, the bees can be more productive as foragers, as nurses taking care of the brood, and as helpers for hygiene control, with less illness and better able to cope with exogenous stressors. In essence, the services that bees provide internally within the hive, and externally for the environment, are substantially augmented utilizing the methods and compositions described within this invention.

Extraction of pure culture, laboratory mycelium on sterilized substrates is substantially different than naturally occurring mycelium form—structurally, quantitatively and qualitatively. Moreover, growing the pure culture mycelium on rice, for instance, a non-native substrate, away from the numerous other co-occurring microbes resident on naturally decomposing wood, produces an arguably different substance than exudates from decomposing wood resplendent with myriads of other organisms (a gram of rotting wood naturally hosts hundreds of other microorganisms, including bacteria protozoa, other fungi, co-inhabiting with or upon the wood decomposing mycelium.). Hence the exudates from the raw mycelium in nature, containing a plurality of organisms, is fundamentally different and are unlikely to benefit bees with the same antiviral and longevity benefits seen with the specifically diluted, pure culture extracts made from mycelium as described in the current invention. In other words, the bees benefit from several alterations and manipulations by the inventor outside of nature: the exudates from the pure culture mycelium must be highly diluted within discrete concentrations to show benefits. After finding the initial extracts to be toxic, most researchers would have abandoned this line of inquiry. Indeed, when the inventor proposed this idea to entomologists and mycologists skilled in the art, they deferred to engage with the inventor as they expected toxicity, and did not want to harm bees. Initial results, ironically, confirmed their suspicions. Some even said my idea was "preposterous" and wanted nothing to do with it.

As with botanicals, it is expected that fungal extracts may be more effective than single constituents or drugs. See, for example, Elfawal et al., Dried whole-plant *Artemisia annua* slows evolution of malaria drug resistance and overcomes resistance to artemisinin, *Proc Natl Acad Sci USA* 112(3): 821-6 (2015).

Only recently, research has discovered that the mycelium has more genes turned on than the mushrooms that ultimately are formed from it. As was noted by Li et al., 2013, The protein-coding genes were expressed higher in mycelia or primordial stages compared with those in the fruiting bodies." Li et al., "Complete mitochondrial genome of the medicinal mushroom *Ganoderma lucidum*." PLoS ONE 8(8):e72038 (2013). doi:10.1371/journal.pone.0072038.

Moreover, the network-like structure of the mycelium allows for epigenetic evolution of strains that can be evolved to emit substances targeted specifically for the benefit of bees. Such improvements are anticipated by the inventor as a method for making strains and compositions more attractive to bees and more appropriate for helping bees overcome CCD.

In essence, the inventor has devised a novel nutraceutical which is rich is a wide array of coumarins, phenols and polyphenols; and anti-viral, anti-fungal, anti-bacterial and anti-protozoal agents, and a wide diversity of specialized metabolites such as antioxidants and antimutagens, which are generated as a result of mycelium digesting grains or wood and are attractive to bees and supportive of their host defense against stressors and diseases. The extracts of mushrooms used medicinally for human health have an unexpected benefit for bee health, including lowering antiviral counts and extending bee lifespans. Indeed, the fungal contribution to propolis and honey, as well as to pollen, augments the immune systems of bees, and by extension to people, on specific, fundamental, complex levels. The inventor notes extracts of mycelium grown on grain inoculated wood are expected to contain more polyphenols, coumarins and compounds that up-regulate detoxification and immunity genes in the bees, as opposed to extracts of mycelium grown via liquid fermentation.

Since nature may require decades, even millennia, before new beneficial associations can be established, with bees unable to react quickly enough to the recent advent of new herbicides, pesticides, fungicides and miticides, we can jump start—jumping ahead of evolution—this process by giving these beneficial fungal species a primary role in the pathways of bee biology and biochemistry to bolster their host defenses and prevent CCD. The chemical composition of fungal mycelium is complex and variable within and among the various mushroom phyla, families and genera, traits that makes fungal extracts a good defense against rapidly evolving pests and pathogens.

Attractants:

One component of the invention is the use of fungal extracts, whereby the extracts are generated from the mycelium of polyporoid, basidiomycetous and ascomycetous species, to attract bees. The bees are attracted to the polysaccharide-rich extracellular and intracellular metabolites secreted by the mycelium. Within these exudates are compounds that attract bees, feed them with sugar rich and other nutrients, provide antiviral, antifungal and antibacterial protection, while bolstering their resistance to pesticides and improving colony health and honey production. In fact, honeys holding these fungal components could proffer medicinal benefits to bees and other animal species, including humans.

These extracellular exudates from, for instance, the King Stropharia or the Garden Giant mushroom (*Stropharia rugoso-annulata*), have an attractive effect on bees, especially during the time when flowering plants of their preference are limited. Bees are attracted both to the extracellular extracts as well as living mycelium. Other non-toxic mushroom species, which may or may not possess antiviral and life extending properties, including gourmet and medicinal mushrooms, are expected to attract bees to varying degrees in a similar fashion.

The pleasant fragrance of *Stropharia rugoso-annulata* out-gassing from the mycelium may attract bees, although no other scientists, to the best of this inventor's knowledge, has ever discovered or stated this. The present inventor has discovered *Stropharia rugoso-annulata* mycelium emits a rich, attracting flower-like essence. Oyster mushrooms in the genus *Pleurotus*, especially *Pleurotus ostreatus, P. pulmonarius, P. lignatilis, P. sapidus, P. eryngii, P. populinus* and other related species emit a pleasing anise-like fragrance, as does *Clitocybe odora*. Another candidate is the split-gill polypore, *Schizophyllum commune*, one of the most common of all woodland Basidiomycetes, which produces a potent, sweet fragrance in culture, at times overwhelming the olfactory senses of lab personnel, and is a source of coumarins and coumaric acids. Interestingly, only those growing *Schizophyllum commune* in mass, in vitro, on cereal grains or wood would ever know about this potent outgassing fragrance. The inventor knows of no one else in his 40 years of experience who has mentioned or reported on this fragrance phenomenon with this species. *Schizophyllum commune* is one of the most prominent white rot, woodland species across the temperate and tropical regions of the world, and creates softened, sweet wood from which bees can benefit. Many other species probably emit attractive fragrances to bees, which are undetectable to humans or not noticeably enticing.

The mycelium from Agaricomycetes and the extracts made from the pure culture mycelium may be the source of new bee attractants. The Agaricomycetes are the only fungi that decompose lignin, and includes the gilled mushrooms, such as *Stropharia rugoso-annulata*, and the polypores, such as those related to *Fomitopsis* species. The Agaricomycetes encompasses—16,000 described species. Many of the Agaricomycetes dually decompose cellulose and lignin. Native bees use rotten logs for nesting, as discussed above in connection with bears, fungi and bees, which the inventor hypothesizes provides bees with the sugar rich and cytochrome P450 coding and up-regulating compounds via water droplets and nectar secreted by the mycelium of Agaricomycetes.

Currently, our regenerated forests have about 10-15% of the wood debris compared to native woodlands! This relatively recent loss of decomposable wood debris limits the availability of these beneficial fungi to native and imported bees, introducing a heretofore unreported, additional stress factor. The continued constriction of debris fields further erodes the food webs essential not only to bees, but also to most organisms that are dependent upon healthy and sustainable ecosystems.

For instance, fungal extracts of the preconidial (pre-sporulation) mycelium of non-Agaricomycetes fungi, including *Metarhizium anisopliae* and *Aspergillus flavus*, have been shown by the inventor to attract Phorid flies (and other insects) (See U.S. Pat. Nos. 6,660,290, 7,122,176, 7,951,388, 7,951,389 and 8,501,207), arresting their migration, and thus prevent these flies from vectoring diseases. Moreover, pathogen hosting mites are also attracted and stopped from moving into the bee colonies using these mycelium-based extracts, thus reducing not only the pathogen payloads mites carry, but also reducing the numbers of mites which might otherwise infect the bees. Similar approaches may be used to control beehive pests, such as the greater and lesser wax moths and the small hive beetle, if needed. Moreover, strains of these pre-sporulation entomopathogenic fungi can be selected for their high thermal tolerance and their abilities for attracting and killing mites and flies which harm bees or vector pathogens. Research into post-sporulation and spore-based *Metarhizium anisopliae* technologies (which may have the disadvantage of repelling mites and/or insects as compared to the attractancy of preconidial mycelium) have demonstrated the relative ease with which strains may be selected for thermal tolerance to high hive temperatures and high pathogenicity and/or mortality to *Varroa* mites. Rodriguez et al., Selection of entomopathogenic fungi to control *Varroa destructor* (Acari: *Varroidae*), Chilean J. Agric. Res., 69(4): 534-540 (2009); Rodriguez et aL, Evaluation of *Metarhizium anisopliae* var. *anisopliae* Qu-M845 isolate to control *Varroa destructor* (Acari: *Varroidae*) in laboratory and field trials, Chilean J. Agric. Res., 69(4): 541-547 (2009); Boyle, New Brunswick Department of Agriculture, Aquaculture and Fisheries, Integrated Pest Management—Compatible Biological Control of *Varroa* Mite of Honey Bee; Fungi help combat honeybee killer, BBC News Science/Nature, Aug. 9, 2002.

Moreover, the inventor has clearly shown that the preconidial mycelium of entomopathogenic fungi, such as but not limited to, *Metarhizium anisopliae, Beauveria bassiana* and *Cordyceps* species, elicit a stimulatory feeding response (phagostimulation) in many insects and other arthropods from the smelling and subsequent ingestion of the extracts made from presporulating (preconidial) mycelium. However, bees show a unique tolerance to the toxins from the spores and mycelium of *Metarhizium anisopliae* that harms mites and phorid flies. Hence having a blend of entomopathogenic fungi, prior to sporulating, or extracts thereof, mixed with the spores (conidia) of these same fungi, could stimulate the bees to consume more mycelia and the extracts thereof, including the beneficial polypore fungi, resulting in a unique suite of synergistic advantages, which includes longevity factors, antiviral, antibacterial and antifungal effects, up-regulations of cytochrome (p450) detoxification pathways, providing complex sugars, vitamins and nutrients, while lessening the toxicity of anthropogenic insecticides, herbicides, fungicides, anthropogenic toxins and also reducing mite and phorid fly populations, all the while introducing fungal species supporting a healthy bee gut bacterial microbiome. Each one of these factors helps bees reduce the stressors of colony collapse disorders. The combination of these benefits within one delivery system—as a composition or a method—is an unprecedented approach, to the best of the knowledge of this inventor. Methods for selecting and optimizing strains within each species will likely result in improvements as each variable is tested and combined.

Humans are limited to perceiving color wavelengths of light from approximately 390 to 750 nanometers (nm). Bees, like many insects, see colors from approximately 300 to 650 nm. Many mushroom species like Oyster mushrooms (*Pleurotus ostreatus*) are triggered into fruiting around 360 nanometers, beyond the far end of our ability to detect. (See Action spectra for Hyphal Aggregation, the first stage of fruiting, in the basidiomycete *Pleurotus ostreatus*, Richartz and Maclellan in *Photochemistry and Photobiology* pages 815-820, May 1987. Mushroom mycelium will absorb some of this light and reflect much of it, due to the limitations of absorption through the translucent, hyaline cell walls of the mycelium.

When mycelium growing deep within wood or the ground reaches the surface of ground or wood, and is exposed to light, a phase change occurs in the mushroom's life cycle, going from mycelium to the first stages of mushroom formation, hyphal aggregation and primordia (baby mushroom') formation. The mycelium in many species will not form primordia unless there is light exposure near to the ultraviolet or 360 nanometer or lower wavelengths. This is well within the range bees can detect but beyond the limits of what humans can.

Attractiveness to mycelium stimulated by blue light invisible to humans but visible to bees is highly significant discovery as bees are most easily trained to associate food in the ultraviolet wavelengths of color. As Menzel and Backhaus determined in 1989, bees could learn faster when the food was associated with violet light as compared to all other colors. Menzel, R. and Backhaus, W. 1989. "Color vision in honey bees: Phenomena and physiological mechanisms". In D. Stavenga and R. Hardie (eds.): *Facets of vision*, Berlin-Heidelberg-New York: 281-297.

Hence, bees finding surfacing mycelium, at the time when nutrients are being up-channeled into the pre-primordia or primordia forming mycelium in response to violet light wavelengths, and when this light is critical for stimulating mycelium to switch into mushroom formation, such detection by bees would be an opportune time to find surfacing mycelium and capture dense nutrition when mycelium is so metabolically active. Although hypothetical and speculative by this inventor, this interaction merits further research since bees can be trained to discover food based on light spectra associations. This added element to this invention can accelerate the learning process of bees for finding new food sources using the attributes of mycelium. As a result, the embodiments of this invention also provide the benefit of enhancing the usefulness and attractiveness of other forms of foods for helping the health of bees using these aforementioned mycelial properties, particularly helping bees discover mycelium at the primordia formation stages.

Surfacing mycelium outgasses carbon dioxide and exudates fragrances, and this inventor hypothesizes that bees can detect mycelium not only from its scent, but are also attracted to the mycelium's response to this blue spectrum light, whereupon mushroom mycelium begins to pack protein, vitamins, and sugar-rich nutrients at the interface between the high carbon dioxide environment within substrates and the highly oxygenated environments just above, and in doing so builds nutritionally dense but accessible primordia—the first stage of mushroom formation or basidiospores formation (as in the case of resupinate polypores like *Inonotus* species, forming exposed hymenial surfaces, or crusts, that are brightly colored such as *Inonotus andersonii*). Many of the brightly colored fungal pigments, especially but not limited to yellowish ones, exhibited by mycelium can be composed of fungal bioflavonoids, many of which are polyphenols. Exploring this rich interface environment—the surface of yellowish fungal mycelial membranes exposed to the atmosphere—is anticipated by the inventor to be a rich reservoir for bees to harvest extracellular and intracellular metabolites endowed with nutrients and immune-supporting compounds, including "mycoflavonoids" and "mycosterols" including phenols and polyphenols not limited to coumarins and benzoic and cinnamic acid derivatives including coumaric acids and their glycosides.

By way of example, but not of limitation, mycelia of some species, especially in the genus *Phellinus* and *Inonotus*, produce brightly colored, yellowish pigments in their mycelium including polyphenols, for example hispolons such as 6-(3,4-Dihydroxyphenyl)-4-hydroxyhexa-3,5-dien-2-one, ($C_{12}H_{12}O_4$), a bright yellow bioactive group of compounds with antioxidant and immune enhancing properties derived from polypore species such as *Inonotus hisipidus* and *Phellinus linteus*. The inventor hypothesizes these bright yellowish-colored mycelia would additionally attract bees foraging for sugars, polyphenols, moisture, natural nutrients and other secretions that have immune-building antiviral, antibacterial, antifungal and antiprotozoal properties. Since bees are especially attracted to yellow colors, those species of fungi, such as *Phellinus* and *Inonotus*, which produce bright yellowish colors, could preferentially attract bees and also are directly associated with the yellowish polyphenols containing coumarins to help bees activate their cytochrome P450 enzyme pathways. This inventor sees the growing of these wood-decomposing species that produce brightly pigmented mycelia as preferred candidates for designing mycelial platforms and extracts for helping bees. Consequently, extracts of mycelium forming primordia and extracts of colored mycelium are preferred bee attractants.

The mycelium in many fungal species will not form sporulating structures, including but not limited to mushroom formation; such fungi are also preferred for studying their mycelial extracts for bee attractancy and health.
Viruses, Fungi, Bacteria and Protozoa:

Bees infected by viruses can lose immune function, as well as the ability to perform other metabolic functions, as a result of the viruses "hijacking" the ribosomal machinery to their benefit, chemically interfering with the crucial phenoloxidase cascade, suppressing immune responses before they are initiated, manipulating the host's immune signaling network, disabling the host's antimicrobial peptides, interfering with the RNAi response and/or creating "superantigens" that can overwhelm the host immune system and otherwise adversely affecting bee health.

The exclusive dependence of viruses on the host cellular machinery for their propagation and survival make them highly susceptible to the characteristics of the cellular environment like short RNA mediated interference. It also gives the virus an opportunity to fight and/or modulate the host to suit its needs. Thus the range of interactions possible through miRNA-mRNA cross talk at the host-pathogen interface is large. These interactions can be further fine-tuned in the host by changes in gene expression, mutations and polymorphisms. In the pathogen, the high rate of mutations adds to the complexity of the interaction network. Viruses either produce micro-RNAs or target host micro- RNAs essential to the host immune system. Scaria et al. (2006) Host-virus interaction: a new role for microRNAs, *Retrovirology*, 2006, 3:68; Oliver, Sick Bees—Part 4: Immune Response to Viruses, American Bee Journal, November 2010.

Mushroom mycelium produces a wide array of compounds that can be anti-bacterial or anti-viral. U.S. Pat. No. 8,765,138 to the inventor discloses the antiviral activity of *Fomitopsis officinalis*, which includes activity against avian flu viruses and herpes simplex I & II. Other viruses are anticipated to be sensitive to the antivirals being coded and expressed by the mycelium of *Fomitopsis officinalis*, and indeed many species in the polyporaceae and Basidiomycetes fungi. The mycelial extracts are active against numerous viruses that harm bees, particularly but not limited to BQCV (Black Cell Queen Virus), IAPV (Israeli Acute Paralysis Virus), DWV (Deformed Wing Virus), TRV (Tobacco Ringspot Virus), and their relatives. The active ingredients limiting viruses within extracts are varied, but two groups are polyphenols including coumarins and sterols including dehydrosulpherinic acids, eburicoic acids and related compounds. Synergistic benefits between these polyphenols and sterols can further boost the host defense of bees. These compounds are resident within the complexes that include fatty acids, lipids and sterols. As such, many other active ingredients related to fatty acids, lipids and sterols having antiviral properties are expected to be of bee benefit. Many of these aforementioned compounds known as bioflavonoids, and the species that produce them, are of interest because some of these species produce mycelium with bright yellowish colors, which may also serve to attract bees. Very little work, if any, has been done by mycologists to detect the "colors" of myceliated wood visible to bees but invisible, or nearly so, to the human eye, especially light reflected in the ultraviolet bands.

The inventor has also discovered the antibacterial properties of *Fomitopsis officinalis* mycelial extracts against staph, tuberculosis and *E. coli* bacteria. This antibacterial activity is likely to confer an additional layer of protection from diseases carried by other organisms. These extracts will similarly have a positive influence in limiting the deleterious effects from known and yet undiscovered bacteria that are harmful to bees, animals and plants. See U.S. patent application Ser. No. 13/998,914 and related applications above.

It is expected that medicinal mushroom species substances useful in humans will similarly prove useful in up-regulating of immune genes and benefitting the bee's immune system. Since many such genes are evolutionarily conserved or similar, it is expected that the extracts of the mycelium of such mushrooms will similarly be useful in up-regulating genes and systems in bees to degrade and deal with infections.

The preferred effective dose varies from species to species, in part because the extracts can be, in common with most medicines, medicinal at low doses and toxic at high doses. In addition, some species such as *Fomitopsis officinalis* may have both strong antiviral effects and a lower toxic threshold as compared to other medicinal species. In general, for all medicinal mushroom species mentioned herein by this inventor, preferred doses range from 0.0001% to 50%, with a more preferred range of 0.001%-25% and a most preferred range of 0.01% to 15%. With many of the polypore extracts in particular, the results in general indicate that the extracts need to be diluted to less than 10%, or less than 1% or less than 0.1% with many of these polypore mushroom extracts, to confer antiviral and longevity benefits to bees. A preferred dose added to liquid or solid bee nutrients for *Fomitopsis officinalis* would be from 0.0001%–0.1%; a preferred dose for *Trametes versicolor* or *Fomes fomentarius* and *F. pinicola*. would be from 0.1% to 10% based on results that show both improved longevity and improved reduction in viral load at 10% concentrations. Except for *Trametes versicolor* and *Fomes fomentarius*, in general 10% concentrations did not help increase bee longevity. Consistently, higher concentrations, above 10% had adverse effects on overall lifespans.

Medicinal mushrooms and the mycelium of medicinal mushrooms are defined as mushroom and mycelium that support health and nutrition. In the context of bees, this includes mushroom and mycelium that has the effect of increasing longevity, increasing foraging abilities, increasing resistance to disease, increasing ability to detoxify anthropogenic toxins, increasing parasite resistance, possessing antiviral, antibacterial and/or antifungal activity, and increasing bees' ability to better withstand stressors associated with the complex collectively called 'colony collapse disorder.'

Useful and preferred fungal genera include, by way of example but not of limitation: the gilled mushrooms (Agaricales) *Agaricus, Agrocybe, Armillaria, Clitocybe, Collybia, Conocybe, Coprinus, Coprinopsis, Flammulina, Giganopanus, Gymnopilus, Hypholoma, Inocybe, Hypsizygus, Lentinula, Lentinus, Lenzites, Lepiota, Lepista, Lyophyllum, Macrocybe, Marasmius, Mycena, Omphalotus, Panellus, Panaeolus, Sarcomyxa, Pholiota, Pleurotus, Pluteus, Psathyrella, Psilocybe, Schizophyllum, Stropharia, Termitomyces, Tricholoma, Volvariella*, etc.; the polypore mushrooms (Polyporaceae) *Albatrellus, Antrodia, Bjerkandera, Bondarzewia, Bridgeoporus, Ceriporia, Coltricia, Coriolus, Daedalea, Dentocorticium, Echinodontium, Fistulina, Flavodon, Fomes, Fomitopsis, Ganoderma, Gloeophyllum, Grifola, Heterobasidion, Inonotus, Irpex, Laetiporus, Meripilus, Oligoporus, Oxyporus, Phaeolus, Phellinus, Piptoporus, Polyporus, Poria, Schizophyllum, Schizopora, Trametes, Wolfiporia*; the toothed mushrooms *Hericium, Sarcodon, Hydnum, Hydnellum* etc.; Basidiomycetes such as *Auricularia, Calvatia, Ceriporiopsis, Coniophora, Cyathus, Lycoperdon, Merulius, Phlebia, Serpula, Sparassis and Stereum*; Ascomycetes such as *Cordyceps, Ophiocordyceps, Morchella, Tuber, Peziza*, etc.; 'jelly fungi' such as *Tremella*; the mycorrhizal mushrooms, fungi such as *Phanerochaete* (including those such as *P. chrysosporium* with an imperfect state and *P. sordida*).

Suitable fungal species and genera include by way of example only, but not of limitation: *Agaricus augustus, A. blazei, A. brasiliensis, A. brunnescens, A. campestris, A. lilaceps, A. placomyces, A. subrufescens* and *A. sylvicola, Acaulospora delicata; Agrocybe aegerita, A. praecox* and *A. arvalis; Albatrellus hirtus* and *A. syringae; Alpova pachyploeus; Amanita muscaria; Antrodia carbonica, A. cinnamomea* and *A. radiculosa; Armillaria bulbosa, A. gallica, A. matsutake, A. mellea* and *A. ponderosa; Astraeus hygrometricus; Athelia neuhoffii; Auricularia auricula* and *A. polytricha; Bjerkandera adusta* and *B. adusta; Boletinellus merulioides; Boletus punctipes; Bondarzewia berkeleyi; Bridgeoporus nobilissimus; Calvatia gigantea; Cenococcum geophilum; Ceriporia purpurea; Ceriporiopsis subvermispora; Clitocybe odora, Collybia albuminosa* and *C. tuberosa; Coltricia perennis; Coniophora puteana; Coprinus comatus, C. niveus* and 'Inky Caps'; *Cordyceps bassiana, C. variabilis, C. facis, C. subsessilis, C. myrmecophila, C. sphecocephala, C. entomorrhiza, C. gracilis, C. militaris, C. washingtonensis, C. melolanthae, C. ravenelii, C. unilat-*

*eralis, C. clavulata* and *C. sinensis; Cyathus stercoreus; Daedalea quercina; Dentocorticium sulphurellum; Echinodontium tinctorium; Fistulina hepatica; Flammulina velutipes* and *F. populicola; Flavodon flavus; Fomes fomentarius, F. lignosus; Fomitopsis officinalis, Fomitopsis cana, F. subtropica* and *F. pinicola; G. resinaceum, annularis, G. australe, G. atrum, G. brownii, G. collosum, G. sinensis, G. lingzhi, G. curtisii, G. japonicum, G. lucidum, G. lucidum* var. *resinaceum, G. neo-japonicum, G. oregonense, G. sinense, G. tornatum* and *G. tsugae; Gigaspora gigantia, G. gilmorei, G. heterogama, G. margarita; Gliocladium virens; Gloeophyllum saeparium; Glomus aggregatum, G. caledonius, G. clarus, G. fasciculatum, G. fasiculatus, G. lamellosum, G. macrocarpum* and *G. mosseae; Grifola frondosa; Gymnopus dryophilus, Gymnopus peronatus, Hebeloma anthracophilum* and *H. crustuliniforme; Hericium abietis, H. coralloides, H. erinaceus* and *H. capnoides; Heterobasidion annosum; Hypholoma capnoides* and *H. sublateritium; Hypsizygus ulmarius* and *H. tessulatus* (=*H. marmoreus*); *Inonotus hispidus* and *I. obliquus; Irpex lacteus; Lactarius deliciosus; Laetiporus sulphureus* (=*Polyporus sulphureus*), *L. conifercola, L. cinncinatus; Lentinula edodes; Lentinus lepideus, L. giganteus, L. ponderosa, L. squarrosulus* and *L. tigrinus; Lentinula* species; *Lenzites betulina; Lepiota rachodes* and *L. procera; Lepista nuda* (=*Clitocybe nuda*); *Lycoperdon lilacinum* and *L. perlatum; Lyophyllum decastes; Macrocybe crassa; Marasmius oreades; Meripilus giganteus; Merulius incarnatus, M. incrassata* and *M. tremellosus; Morchella angusticeps, M. crassipes* and *M. esculenta; Mycena citricolor, M. alcalina* and *M. chlorophos; Omphalotus olearius; Panellus stypticus, P. serotinus; Paxillus involutus; Phaeolus schweinitzii; Phellinus igniarius, P. pini, P. linteus* and *P. weirii; Pholiota nameko, P. squarrosa, Piloderma bicolor; Piptoporus betulinus; Pisolithus tinctorius; Pleurotus citrinopileatus* (=*P. cornucopiae* var. *citrinopileatus*), *P. cystidiosus*, (=*P. abalonus, P. smithii*), *P. djamor* (=*P. flabellatus, P. salmoneostramineus*), *P. dryinus, P. eryngii, P. lignatils, P. euosmus, P. nebrodensis, P. ostreatus, P. pulmonarius* (*P. sajor-caju*) and *P. tuberregium; Pluteus cervinus; Polyporus indigenus, P. saporema, P. squamosus, P. tuberaster* and *P. umbellatus* (=*Grifola umbellata*); *Psathyrella hydrophila, Psilocybe allenii, aztecorum, P. azurescens, P. baeocystis, P. bohemica, P. caerulescens, P. coprophila, P. cubensis, P. cyanescens, P. hoogshagenii, P. mexicana, P. ovoideocystidiata, P. pelliculosa, P. semilanceata, P. serbica, P. subaeruginosa, P. tampanensis* and *P. weilii; Rhizopogon nigrescens, R. roseolus* and *R. tenuis* (=*Glomus tenuis*); *Schizophyllum commune; Schizopora paradoxa; Sclerocytis sisuosa; Serpula lacrymans* and *S. himantioides; Scleroderma albidum, S. aurantium* and *S. polyrhizum; Scutellospora calospora; Sparassis crispa* and *S. herbstii; Stereum complicatum* and *S. ostrea; Stropharia ambigua, S. aeruginosa, S. cyanea, S. albocyanea, S. caerulea, S. semiglobata, S. semigloboides*, and *S. rugoso-annulata; Suillus cothurnatus; Talaromyces flavus; Termitomyces robustus; Trametes elegans, Trametes T. gibbosa, T. villosa, T. cingulata, T. hirsuta, T. suaveolens* and *T. versicolor; Trichoderma viride, T. harmatum; Tricholoma giganteum* and *T. magnivelare* (Matsutake); *Tremella aurantia, T. fuciformis* and *T. mesenterica; Volvariella volvacea*; and numerous other beneficial fungi.

Preferred strains which have shown exceptional characteristics useful for the practice of this invention, include, by way of example but not of limitation, *Fomes fomentarius* (NY state), *Ganoderma applanatum* (Strain Duckabush), *Fomitopsis officinalis* (Strains I, VI, X), *Fomitopsis pinicola* (Strain I), *Ganoderma oregonense* (Meadow Lake), *Heterobasidion annosum* (Dosewalips), *Pleurotus ostreatus* (Strains PW-OST, Nisqually), *Psilocybe azurescens* (Stamets strain), *Stropharia rugoso-annulata* (Strain F), *Trametes versicolor* (Kamilche Point) and *Inonotus obliquus* (Stamets NY).

Additional suitable mushroom genera and species can be found in standard mycological field guides such as *Mushrooms Demystified* (1979, 1986) by David Arora, *The Audubon Society Field Guide to North American Mushrooms* (1981, 1995) by Gary Lincoff, and *Psilocybin Mushrooms of the World* (1996) by Paul Stamets. Continually updated lists of suitable species based on the most recent DNA analysis can be found at the Tree of Life and Encyclopedia of Life (EOL) web projects.

The extracts from the mycelium of *Fomitopsis officinalis* particularly, *Inonotus obliquus, Fomes fomentarius, Ganoderma resinaceum* and other species in the Polyporaceae generally, reduce the pathogenicity of viruses to bees by directly reducing the viral particle populations while also fortifying the immune systems of bees, thus limiting their virulence and transmissibility. Moreover, bees better benefit from a combination of a mixture of the antiviral components generated by the mycelium with the antimicrobial properties of coumarins and other compounds produced by the *Fomitopsis officinalis* mycelium. The extracellular exudates secreted by the mycelium of the beneficial fungi described herein have a combination of these constituents, but balanced to have the net benefit of attracting bees so they are fortified with immune enhancing, and nutritionally beneficial constituents. This multifaceted effect results in fortifying the immune systems of bees and their colonies, making them less susceptible to viral, bacterial, protozoal and fungal mitigated diseases.

The present inventor has found that *Ganoderma, Fomes, Fomitopsis, Fomitoporia, Ganoderma, Antrodia, Inonotus, Irpex, Lenzites, Phellinus, Sparassis, Hypholoma, Pleurotus, Schizophyllum*, and *Stropharia* species demonstrate strong anti-fungal properties and expects these will also be useful for controlling fungal pathogens afflicting bees, including but not limited to *Nosema* species and other pathogenic microsporidia, Chalkbrood and Stonebrood.

The first antiviral from a mushroom ever discovered was from the "Ice Man" polypore, *Fomes fomentarius*, against the Tobacco Mosaic Virus, the first virus ever to be discovered, and related to the Tobacco Ringspot Virus. This polypore mushroom is a saprophyte on birch, beech and other temperate deciduous hardwoods. When it grows, the wood is softened, releasing moisture, insect-attracting fragrances and sweetened with the rich, complex polysaccharides, as well as proteins and other substances generated by the mycelium of this fungus. This fungus attracts beetles whose burrows subsequently can be occupied by native bees. In essence, this is one example of what the inventor anticipates to be many examples of the role polypore and other Basidiomycetes fungi play in providing bees with nutrients. Interestingly, *Fomes fomentarius* is a known endophyte of birch trees—meaning that they are part of the tree's natural immune system. The inventor hypothesizes that many of these endophytic fungi confer antiviral properties on plants and bees—if encountered within a discrete, diluted window, as well as other insects, as they forage or nest in wood hosting these fungi. But, if encountered in their pure form, many of these may, in fact, be toxic. Here is where human intervention can help evolve a bridge of antiviral benefits otherwise unlikely encountered in nature. The inventor believes the inter-relational dimensions wherein the biology of bees, fungi and decomposing trees and plants all intersect will become a fertile area of scientific research for helping and evolving ecosystems for decades to come.

The aggressive wood rotting fungi listed in this application compete with many other fungi to establish their dominance in ecological niches. The polypore mushroom species, in particular species of *Antrodia, Fomes, Fomitopsis, Ganoderma, Grifola, Heterobasidion, Inonotus, Stereum* and *Trametes*, produce anti-fungal properties, present in extracts, which this inventor suggests will be effective against *Nosema*, a microsporidium fungal parasite plaguing bees worldwide.

Of course, bears are not the only way to spread to trees *Fomitopsis* and other fungi that may improve bee heath. Any activity resulting in creating wounds in trees, or in creating dead wood, creates a potential fungal platform of bee benefit. The human use of woodchips as 'beauty bark' or for making trails, or as a top dressing around ornamentals, would also serve to create a mycelial platform of benefit to bees. Ultimately, this means we can grow the mycelium of these fungi, en masse, in a pre-sporulating or pre-conidial state, make mycelial 'landing pads' for bees, or make extracts, and in doing so creating a new generation of bee attractants and nutrition customized accordingly.

With these hypotheses in mind, the inventor sees use of a wide array of Basidiomycetes, wood-decomposing fungi to develop a fungal bioshield, a "bee bioshield" of protection from the stressors leading to colony collapse disorder.

Moreover, the antibiotic effect of these extracts on microsporidium bee parasites, particularly *Nosema apis*, the cause of '*Nosema*,' recently reclassified as a simple fungus, will prove to be a beneficial co-occurring factor.

Another advantage of the present invention is the wide-ranging antiviral, antibacterial and antifungal properties derived from mycelium. Many of the inventor's mycelium extract fractions demonstrate antiviral activity even when the bioguided fractionation pathway led to antibacterials. Microbial agents are often thought of as microbial-type specific (there is some cross-over between antibacterials and anti-parasitics and now may even be at least one class with both anti-bacterial and anti-fungal activity), but considering how difficult it is to attain anti-viral specificity alone, and the absence of known shared molecular targets between bacteria and viruses that also exhibit any degree of selectivity with respect to the host, broad anti-microbial activity is rare. Without being bound to any theory, the inventor would hypothesize that the extracts are acting as immuno-stimulators, immuno-potentiators and immuno-regulators with antiviral, antibacterial and antifungal effects.

It is hypothesized that the mycelial components discussed above and/or other known and unknown compounds are anti-bacterial and anti-fungal, helping immunity, and hence the interaction between bees and extracts of pure cultured mycelium within discrete concentrations is an unanticipated advantage of the present invention.

*Hyphodermella corrugata, Polyporus umbellatus*, and *Piptoporus betulinus* are species of the polyporales known to the author from his research to exhibit strong antiprotozoal properties. Agaric acid is thought to be one agent responsible for *Piptoporus betulinus*'s anti-protozoal activity. Agaric acid is also produced by *Fomitopsis officinalis*, and possibly by other species in the polyporales. The production of acanthocytes by *Stropharia rugoso-annulata*, known to kill nematodes, may also provide antiprotozoal and antimiticidal benefits to bees. As such, these species and their relatives would be preferred for testing for antiprotozoal activity and up-regulation of antiprotozoal genes in bees.

Pesticides:

As bees are limited in the number and variety of enzymes needed to denature natural and anthropogenic toxins, these toxins impair their baseline immunity, making them more susceptible to pathogens from numerous vectors—from *Varroa* mites, *Nosema* and microsporidia fungi, Phorid flies, and the viruses and bacteria they carry. By increasing the bees' ability to degrade these toxins by up-regulation of more cytochrome P450 genes, GST genes and/or CCE genes, the bees' immune state is improved to better resist these assaults and other stress factors. Moreover, by providing bees with a blend of fungal extracts that specifically limit the severity of assaults from Phorid flies, *Varroa* mites, *Nosema* fungi and viruses, bee colony health can be fortified for the long-term health of the brood, the workers, the queen and her drones. These fungal components are naturally incorporated into the honey and propolis, thus imparting an advantage to developing generations. Ultimately, not only are bees are protected, but honey production is expected to increase, and the quality of the honey better supports downstream generational health and survivability.

Those mushroom species useful in bioremediation ("mycoremediation") of toxins, pollutants and pesticides and extracts of their mycelium are expected to contain various substances useful in turning on, up-regulating and modulating the genes necessary for the biodegradation of pesticides. Since many such genes, or the systems such as the cytochrome system, are evolutionarily conserved or similar, it is expected that the extracts of the mycelium of such mushrooms will similarly be useful in up-regulating genes and systems in bees to degrade and deal with such pesticides. Useful and preferred species include the saprophytic mushrooms *Pleurotus ostreatus* and other *Pleurotus* species, *Trametes versicolor, Trametes elegans* and other *Trametes* species, *Fomes fomentarius, Fomitopsis officinalis* and *F. pinicola, Ganoderma lucidum, G. annulare, G. brownii, G. collosum, G. lingzhi, G. curtisii, G. oregonense* and *G. tsugae; Heterobasidion annosum, Inonotus obliquus, I. hispidus, Irpex lacteus, Laetiporus sulphureus, L. conifericola, L. cincinnatus, Polyporus umbellatus, Polyporus elegans, Polyporus squamosus, Antrodia* species, *Phaeolus schweinitzii, Boletus mirabilis, Gymnopus peronatus, Mycena alcalina, M. aurantiadisca, M. haematopus, Psilocybe azurescens, P. allenii, P. subaeruginosa, P. ovoideocystidiata, P. cubensis, P. cyanescens, Panaeolus cyanescens, Stropharia ambigua, Stropharia rugoso-annulata, Stropharia coronilla, Hypholoma capnoides, H. fasciulare, H. aurantiaca* and other species in the Strophariodeae and Strophariaceae, *Lenzites betulinus, Pholiota adiposa, Pholiota terrestris, Pholiota nameko, Agrocybe aegerita, A. praecox, A. arvalis, Collybia tuberosa, Collybia, Psathyrella hydrophila, P. epimyces, Marasmius oreades*, and their associated, numerous "satellite genera" as well as the other gilled and polypore genera and species known to the mycological science as primary and secondary decomposers of cellulose and lignin.

The mycelium of *Stropharia rugoso-annulata, Fomitopsis officinalis, Fomitopsis pinicola, Schizophyllum commune, Trametes elegans, Trametes versicolor* species and many polyporoid and gilled basidiomycetes produce bioflavonoids, phenols and polyphenols, including coumarins and coumaric acids (both trans- and cis-o- and p-coumaric acids) which up-regulate genes in bees which code for cytochrome P450 enzymes as well as other enzymes critical for digestion, metabolism and toxin destruction. The effect of these mycelial components such as coumarins, p-coumaric acid, o-coumaric acid or their glycosides, is that they turn on more genes within bees which allow for the bees to detoxify a wide range of toxins, particularly insecticides, miticides, herbicides, fungicides and pesticides, and augment the bee's innate immunity.

P-coumaric acid, found in both grains and lignin, is a monomer of sporopollenin, the principal constituent of pollen cell walls and propolis, the resinous compounds gathered and processed by bees to line wax cells. P-coumaric acid is essential for increasing laccase in wood rotting fungi, a cellulase enzyme that breaks down lignin in wood, creating derivative compounds palatable to insects as food, as well as creating habitats (bees can take up residence in tunnels bored by mycophagous beetles). As fungi rot wood, breaking down lignin, they also weep water, rich in these p-coumaric and nutraceutical compounds beneficial to bees. The more p-coumaric acid, the more laccases expressed by the mycelium, the more the wood rots, the more fungal polysaccharides (sugars) and ultimately the more these compounds will be in the fungal exudates that the bees seek and from which they benefit. That wood rotting fungi produce p-coumaric acids and coumarins that can be bio-converted into p-coumaric acids is yet another advantage of this invention.

As was noted by Terrón et al., structurally closely-related aromatic compounds have different effects on laccase activity and on Icc gene expression in the ligninolytic fungus *Trametes* sp. 1-62, *Fungal Genet. Biol.*, October 2004; 41(10):954-62: "Nine phenolic compounds (p-coumaric acid, ferulic acid, guaiacol, syringol, p-methoxyphenol, pyrocatechol, phloroglucinol, 3,5-dihydroxybenzoic acid, and syringaldazine) were tested for their ability to increase laccase production in the ligninolytic basidiomycete *Trametes* sp. 1-62. All these compounds resulted in increases in laccase activity, with the highest levels being detected in the presence of p-coumaric acid (273-fold) and guaiacol (73-fold)."

Interestingly, many of the grains preferred for mycelial spawn production for mushroom industry (see *Growing Gourmet & Medicinal Mushrooms* by the inventor, Paul Stamets, 1993, 2000, Ten Speed Press, Berkeley) are also rich sources of p-coumaric acids and may be useful in bee attractant compositions. The primary phenolic acids in rice grain were identified as p-coumaric acid, ferulic acid, and sinapinic acid.

P-coumaric acid is not only in the grains preferred for mushroom spawn production but they are also generated during the normal life cycle of mushrooms, especially prior to primordia formation. P-coumaric acid is a potent inhibitor of tyrosinase, the enzyme essential for melaninization. The presence and abundance of p-coumaric acid interferes with the production of darkly colored pigments. Ultraviolet light stimulates the photodecomposition of p-coumaric acids, enabling melanization and triggering primordia formation. Once primordia forms, p-coumaric acids degrade into p-hydroxybenzoic acid. Sachan et al., Transforming p-coumaric acid into p-hydroxybenzoic acid by the mycelial culture of a white rot fungus *Schizophyllum commune*, 2010, *African Journal of Microbiology* 4:267-273. As an example, but not one of limitation, the mycelium of *Auricularia auricula* (*A. auricularia-judae*), when grown in culture is whitish and lacks melanin but contains p-coumaric acids. When the mushroom mycelium is exposed to light, the mycelium bio-transforms to create dark brown fruitbodies, which are higher in melanin as they mature, with p-coumaric acids, an inhibitor of melanin, concurrently declining. This is one example and a strong argument for the benefit of using lightly colored mycelium, pre-melaninization as a source of mycelium for making extracts beneficial to bees due to its innate p-coumaric acid content compounded by the native content of p-coumaric acids in the grains that are used for spawn production for growing mycelium. Interestingly, the ideal interface for capturing the best benefits from mycelium for its nutraceutical and p-coumaric acid contents, is short window, often of just a few days in length, before and directly after light exposure, but before dark colored fruitbody development beyond the white primordial stage.

Given that some of the most abundant laccase producers yet tested thus far are *Ganoderma lucidum*, *Trametes versicolor* and *Pleurotus ostreatus*, these species are specifically preferred for use in creating bee-beneficial mixtures.

When not immunologically depressed from man-made and natural toxins, bees natural host defense can better protect bees from other deleterious agents, including viruses and pathogens transmitted by *Varroa* mites.

As our knowledge of the many derivatives of this overarching invention expands, the inventor anticipates that individual fungal species will offer a unique set of benefits. Some will be more antiviral. Some will activate the detoxification pathways in bees better than others against different toxins. Some emit fragrances greater in their attractive properties. As such, blends or "fungal cocktails" of species can be customized according to the needs of the bees, the bee keepers, based on their desired targeted benefits, the ecosystem particulars, and conditioned upon the availability of basic materials.

For example, critical to the bee industry is the protection and generation of new queens. Queens are bred and reared by specialty breeders who are at risk from mites transmitting the Black Queen Cell Virus (BQCV). Finding a selective antiviral to protect queens is another major advantage of this invention. For queen breeding and rearing, both *Inonotus obliquus* and *Ganoderma resinaceum* are very active antiviral additives in reducing Black Queen Cell Virus (BQCV) but not as active against Deformed Wing Virus (DWV), whereas other species are more active against DWV. A blend of two or more mushroom species is therefore preferred to provide a broad bioshield of antiviral activity to protect bees.

Varroa Mites and Insect Parasites:

The inventor has received several patents on compositions and methods of using the presporulating mycelium of entomopathogenic fungi as an attractant and treatment for controlling insects, and more broad patents are pending (U.S. patent application Ser. No. 13/986,978) on arthropods, and the diseases insects and arthropods vector (U.S. patent application Ser. Nos. 13/317,613 and 13/373,719). *Varroa* mites are known as a vector of the Israeli Acute Paralysis Virus and the Tobacco Ringspot viruses. *Varroa* mites, both plant and insect biting mites, carry more than one virus or bacterial pathogen, meaning that mites are one, albeit significant, vector carrying and introducing multiple pathogens in the onslaught threatening beehive health. As bees weaken from viral exposure, for instance, they are less able to shed the attaching *Varroa* mites. However, the mycelium of entomopathogenic fungi, particularly *Aspergillus flavus*, *Metarhizium anisopliae* and *Beauveria bassiana*, can be used to attract, sicken or kill the *Varroa* mites, reducing their activity, delivery of pathogen payloads and numbers, thus tilting the balance in improving the host defense of the colony against CCD. Spores of entomopathogenic fungi, including *Metarhizium*, *Beauveria* and the Entomophthorales can similarly be used to sicken or kill *Varroa* mites, although mites may find spores repellant as compared to preconidial mycelium.

Moreover, extracts of *Metarhizium anisopliae* can be made specifically to attract, but not kill insects, including bees, by growing strains of *Metarhizium anisopliae* that do not contain destructins, or have reduced levels of these or other toxins, or reduced virulence and pathogenicity. Variability of toxins is true when comparing many strains of *Aspergillus flavus*, a known entomopathogenic fungus, primarily toxic due to its aflatoxin content. Aflatoxin-free strains of *Aspergillus flavus* are available currently, which are naturally occurring or can be made through culture selections or genetic modifications. So too can destructin-free strains of *Metarhizium anisopliae* strains be created, selected for, or sourced from natural genomes. Strains can also be produced which are not entirely free of destructins or alfatoxins, but produce such low levels that they can be toxic to mites but not very toxic to bees due to the fact that the bees' cytochrome P450 levels and pathways have been enhanced from exposure to the coumarins and other polyphenols presented by the mycelium. In essence, the up-regulation of cytochrome p450's (CYP's) may help bees better tolerate or detoxify destructins or aflatoxins to which the bees are exposed from *Metarhizium anisopliae* and *Aspergillus flavus* and other toxins produced by entomopathogenic fungi.

The advantage of a destructin-free or a reduced destructin strain of *Metarhizium anisopliae* is that the extracts of the mycelium could be produced with high sugar and terpene content which would simultaneously attract bees and mites. Use of an appropriately sized mesh screen or barrier or other means of selection allows for mites to be partitioned from bees so both bees and mites could be initially attracted to the same location of the extracts (or similarly attracted to preconidial mycelium). The proportionality of the endemic entomopathogenic toxins can be balanced to sicken mites but not bees. Using single or multiple fungal extracts as described herein offers a latitude and flexibility of customized design, so that numerous devices, delivery systems, compositions and methods can be made available for the first time to favor bee health and decrease CCD. Phorid flies, gnats and mites predating on mushrooms are well known to the mushroom industry. What was not known is that extracts of entomopathogenic fungi prior to sporulation are attractive to these insects and arthropods. The present inventor does not believe that hydroethanolic extracts of mushrooms or mushroom mycelium with these attractive properties were known to the mushroom industry prior to this inventor's disclosures in pending and approved patents.

Combining oxalic acids with sugar enriched water loaded with spores or preconidial mycelia of entomopathogenic fungi such as *Metarhizium anisopliae* and *Beauveria bassiana* will improve the miticidal actions of the combination of oxalic acids and entomopathogenic fungi and the anti-miticidal properties of other components resident or added to sugar water, pollen patties or bee sprays, for instance. However, oxalic acid is reactive to the minerals in the fungal extracts, and this poses a hurdle for effective formulation.

When combining oxalic acids with the extracts of filamentous Basidiomycetes fungi, the resident minerals (calcium, phosphorus, iron) may bind with the oxalic acid thus reducing the mineral scouring, miticidal potential of the oxalic acids. Therefore, demineralization of the fungal extracts before combining oxalic acid to the fungal extracts is an embodiment of this invention. Demineralization employs any of numerous methods useful for demineralizing of the fungal extracts so as to prevent conversion of the reactive oxalic acid into water insoluble salts by eliminating calcium and other minerals resident within the fungal extracts. One method of many available is to make use of ion exchange resin technologies. The fungal extracts can be added to distilled water at a ratio of 1:10 preferably, with ranges of 1:1 being the most concentrated and 1:100 being most dilute but less preferable. Upon completion, minerals in the fungal extracts, which would otherwise neutralize the anti-miticidal properties of oxalic acid, will be largely if not completely removed. Thereupon, oxalic acid can be added to the reduced mineral, fungal extracts in a sufficient quantity to have an anti-miticidal effect, in the range of 1-10% of oxalic acid to the mass of the solution, resulting in a low pH in the 0.5-3.5 pH range, with an optimal range in the 0.5-2.0 pH range.

"We seek to understand the botanical sources and biological activities of resins in the field and how resin foraging behavior changes in response to environmental factors, such as infection and other biological stresses. If we can discover plants with preferable and more antimicrobial resins in different regions, it should be possible to better create environments that promote bee health by supporting behaviors and managerial strategies that lead to natural disease resistance." Wilson et al., Metabolomics reveals the origins of antimicrobial resins collected by honey bees. *PLoS One* 8(10): e77512, page 11. The present inventor suggests that pure cultured fungi and fungal mycelium, including fungal attractants, fungal entomopathogens, fungal immunostimulators, fungal antivirals, antibacterials and antifungals can similarly support bee health and lead to natural resistance to diseases and pesticides. Ecosystems and economies benefit from bees that would otherwise suffer without these myco-remedies.

This inventor also anticipates that pollinating insects and animals (bats) will also benefit from the effects of this invention. It is also expected that birds may similarly benefit from similar integrated fungal solutions via addition to nectar feeders and bird foods through the up-regulation of immunological and detoxification genes as well as receiving antiviral benefits, thus extending longevity.

Filamentous, basidiomycetous fungi are also sources of neuroregenerative compounds. Species of *Hericium* (including but not limited to *Hericium erinaceus, Hericium corralloides* and *Hericium abietis*) produce potent nerve growth factors causing regeneration of myelin on the axons of nerves and nerve regeneration. See Stamets, Lion's Mane: A Mushroom That Improves Your Memory and Mood?, The Blog, Huffington Post Healthy Living, Aug. 8, 2012. Psilocybin and psilocybin-producing fungi, including but not limited to species of *Psilocybe, Panaeolus, Gymnopilus, Pluteus* and *Conocybe* such as *Psilocybe azurescens, Psilocybe cyanescens, Psilocybe allenii, Psilocybe cyanofibrillosa, Psilocybe cubensis, Psilocybe ovoideocystidiata, Psilocybe subaeruginosa, Copelandian Panaeoli* (*Copelandia cyanescens, Copelandia tropicalis, Copelandia bispora*), *Pluteus salicinus, Gymnopilus luteofolius, Gymnopilus spectabilis, Conocybe cyanopus* and *Conocybe smithii* can trigger neurogenesis. (See Catlow et al., Effects of psilocybin on hippocampal neurogenesis and extinction of trace fear conditioning, *Exp Brain Res* (2013) 228:481-491 DOI 10.1007/s00221-013-3579-0). Individually or in combination, mixtures of extracts of psilocybin mushroom and *Hericium* mushroom fruitbodies, or more preferably their mycelial extracts, could help repair neurons damaged by toxins, cholinergic pesticides, oxidation, old age, or other sources of neurotoxins. The net effect of ingesting these mixtures of nerve regenerating *Hericium* and psilocybin species would improve the neurological health of bees through neurogenesis and re-myelination, and indeed of animals, including humans. Another, improved form of "mycological honey" might incorporate these elements for the benefits of bees and people, improving cognition, preventing or repairing neuropathies presenting themselves as diseases to humans within scope of the definitions for Alzheimer's, Parkinson's, Parkisonisms, MS (multiple sclerosis), or as yet uncategorized forms of neurological impairment. Indeed such combinations could increase intelligence, sensory abilities, memory, reflexes, reaction times, and problem solving abilities. As such a 'smart mycological honey' is anticipated to be within the scope of this invention.

Ganoderma lucidum is one of the species of particular interest (along with Ganoderma resinaceum, Ganoderma applanatum, Ganoderma brownii, Ganoderma curtisii, Ganoderma oregonense, Ganoderma tsugae, Ganoderma lingzhi, Ganoderma capense, Ganoderma annularis, and Ganoderma collosum) to the inventor as it not only has strong antiviral properties, but has complexes of sugars that result in its mycelium producing a viscous syrup-like "mycological honey" that can be used to help bees survive CCD. The inventor and his team at Fungi Perfecti, LLC have also noted that the extracts of Ganoderma resinaceum will not freeze, even when freeze driers achieve temperatures less than −50 C.° under high vacuum, whereas species tested outside the genus Ganoderma readily freeze dried into a dried state under the same conditions. The inventor hypothesizes the mycelial extract of Ganoderma resinaceum, and likely extracts of related Ganoderma species, maintains a liquid state even under cryogenic conditions due to its unique assortment of complex sugars, sterols, and glycoproteins binding to form a unique liquid matrix far different than any other species tested. This extract may have potential as an anti-freeze with broad reaching implications for medicine, avionics, space travel, and usefulness under extreme temperature conditions for lubricating, preservation, and extremophile chemistry.

In all of the following examples, the inventor anticipates, as derivatives of his discovery, that bioguided fractionation methods will lead to increasing the potency, increasing efficacy, and reducing the cost of production, manufacturing, and the implementation of said inventions and its many elaborations, which become obvious subsequent to this paradigm shifting discovery.

Example 1

Fomes fomentarius, Fomitopsis officinalis, Fomitopsis pinicola, Ganoderma resinaceum, Inonotus obliquus, Piptoporus betulinus, Trametes versicolor, Schizophyllum commune and other mushroom species are cultured and the mycelium grown on rice, barley, flaxseeds or other grains, agricultural debris, or forest products such as sawdust or wood chips (for a list of substrates, See Stamets, Growing Gourmet and Medicinal Mushrooms, 1993, Ten Speed Press, Berkeley, Calif. and Stamets & Chilton, The Mushroom Cultivator, Agarikon Press, Olympia, Wash.). When the mycelium reaches a mass of growth (preferably after 5 to 60 days growth in fermentation or in solid state fermentation subsequent to inoculation, but well before fruitbody formation) mycelial mass can be extracted through simple aqueous, water/ethanol (both of which are preferred) or ethanol washing of the substrate, or from compression of the substrate, all of which will result in a liquid fluid or capture-able extract including extracellular exudates. These extracts can be utilized as they are, or alcohol (25-50% by volume) may be added to aqueous extracts as a preservative and solvent (which will precipitate water-soluble polysaccharides). The hydroethanolic extract can be evaporated or removed, or the alcohol and water may be evaporated and removed separately. The crude extract can be cell free filtered using a 0.12-0.20 μm filter. This extract can be frozen or dried for future use. Alternatively, non-aqueous or non-ethanolic solvent extracts such DMSO, ethyl acetate, ether and other solvents or combinations of solvents known to the art may be utilized, or subcritical or supercritical fluid extracts utilizing, for example, carbon dioxide or water, and optional co-solvents such as alcohols, may be utilized, or microwave-assisted extracts may be utilized.

The extract can be added to any form of feed stocks for bee consumption. The original extract can be used directly or diluted and added to their drinking water, sugar water, bee candy, honey, propolis, pollen patty, grease patty and protein supplements to give improved bee feeds and nutritional products and improved pollen supplements, dietary supplements, feeding supplements and nutritional supplements. The extracts may also be incorporated into sprays used to spray beehives, beehive components, sticky strips, bees and plants and incorporated into the wax used for making combs and supers. Ingestion and contact by bees improves the bees' ability to build immunity through up-regulating of toxin degrading enzymes, reduces pathogen payloads and provide a healthy source of diverse sugars, amino acids, vitamin B's, and nutrients. Moreover, the precipitate, although partitioned from the supernatant, contains within it nutrient rich, and antiviral, health supporting properties, which can be used also as feedstock for benefitting bees. Both the supernatant and the precipitate can be combined, and enzymatically converted using amylase and other enzymes to further transform starches and other ingredients into a more effective composition.

Example 2

The medicinal mushroom mycelium is grown utilizing liquid culture techniques. Whereas growing on rice might have 30-40% conversion of rice to mycelium, liquid vat culture may have essentially complete conversion with >3× more mycelium per unit mass. Hence the liquid vat culture of mycelium and its extracellular metabolites will be easier to utilize in the development of this invention as the process of using vat culture eliminates the need to remove non-metabolized substrate ingredients.

Example 3

To make the mycelial extract, use equal volumes of mycelium grown on grain (barley, flaxseed, rice, oats, millet, wheat, rye, corn), seeds, including nuts, sawdust or wood chips (Douglas fir, pines, oaks, birches, cottonwoods, olives) and immerse into a 50:50 water-ethanol solution. Allow to sit at room temperature for two weeks, and then press to expel the liquid extract. Over several days, a precipitate will fall out of the hydroethanolic solution. The hydroethanolic supernatant is drawn off above the pasty precipitate. After several more weeks, or by using a centrifuge, the precipitate further concentrates into a semisolid state. These wet semisolids are removed and heated to 50° C. for 6-8 hours while stirring. The wet volume of semisolids is reduced to about 40% of the original wet semisolids. The drying down of the semi-solids into the caramel "honey-like" substance yields about 16% of the original wet solids wet. Therefore, using 1000 mL of wet solids (which was 40% of the initial extract) yields about 170 mL of thick syrupy caramel like substance. Continued heating and stirring concentrates this substance with noticeably sweeter properties. The extract can be crystallized, powdered, and used as amendment to other treatments. The liquid, semisolid and crystallized forms are noticeably sweet in taste and could be considered a medicinal candy-like substance useful to both bees and people in a wide number of applications.

Example 4

A mycelial extract is made by extracting fruitbodies or mycelium of basidiomycetous fungi including *Ganoderma resinaceum* in hot water (80-100° C.) for several hours and combined with the room temperature (10-30° C.) water extraction of *Fomes fomentarius, Fomitopsis officinalis, Fomitopsis pinicola, Ganoderma resinaceum, Inonotus obliquus, Piptoporus betulinus, Trametes versicolor* and/or *Schizophyllum commune* mycelium grown on grain or wood. To these water extracts, ethanol is added to make the solution greater than 22% EtOH (ethanol), preferably 35-45% EtOH. Upon addition of ethanol, polysaccharides precipitate out of solution and settle at the bottom of the extraction vessel. Upon drawing off the supernatant, the precipitated polysaccharides, rich in glycosides, glycoproteins and other 'nectar-like' nutrients, are collected and heated between 50-70° C. over several hours, resulting in the creation of a sweet residue attractive to and beneficial to bees. Alternately, the supernatant can be stored over several days, which further yields useful precipitating polysaccharides. These precipitates contain complex sugars, antivirals, antibacterials, cytochrome p450 up-regulating coumaric acids and coumarins, and can be combined with other ingredients used in the feeding water, pollen patties, propolis, bees wax, sprays, or in any delivery system whereby bees make contact with these precipitates, helping bees overcome stressors associated with colony collapse disorder.

Example 5

A mycelial extract made from extracting fruitbodies or mycelium of basidiomycetous fungi including *Ganoderma resinaceum* is first soaked in 100% ethanol (1:1 ratio by mass) for 1-7 days. Upon draining off the ethanol, the mushroom- or mycelial-marc is immersed into hot water (80-100 C) for several hours and combined with the room temperature (10-30 C) water immersion and extraction of *Fomes fomentarius, Fomitopsis officinalis, Fomitopsis pinicola, Ganoderma resinaceum, Inonotus obliquus, Piptoporus betulinus, Trametes versicolor* and/or *Schizophyllum commune* mycelium grown on grain or wood. To these water extracts, the ethanol extracts previously described are added to make the total combined solution greater than 22% EtOH, preferably 35-45% EtOH. Upon addition of ethanol fraction, polysaccharides precipitate out of solution and settle at the bottom of the extraction vessel. P-coumaric acid, being more soluble in ethanol than water, is richer in the ethanolic extracted supernatant. (The ethanolic supernatant, with concentrated p-coumaric acids, is a reservoir of bee-beneficial p450 coding compounds.) This hydroethanolic supernatant can be stored over several days, which further yields a mixture of polysaccharides but which is proportionately higher in p-coumaric acids than the hot water fractions alone. The precipitate also holds p-coumaric acids, and additionally other nutrients, which can be used to feed bees. These p-coumaric enriched precipitates also contain complex sugars, antivirals, antibacterials, and families of coumarins, and can be combined with other ingredients, such as the water soluble mushroom polysaccharides, corn syrup or sugars used in sweetening the feeding water, or additionally incorporated as an ingredient in pollen patties, propolis, bees wax, sprays, or in any delivery system whereby bees make contact with these precipitates, helping bees overcome stressors associated with colony collapse disorder.

Example 6

For each type of mycelium extract (mushroom species), mixed aged honey bees from a single hive were collected on a single day and distributed at random into 16 cages of roughly 100 bees each. Each set of 16 consisted of four control cages (fed sugar syrup), four low concentration cages (fed mycelium extract in sugar syrup at 0.1% v/v), four medium concentration cages (fed mycelium extract in sugar syrup at 1% v/v), and four high concentration cages (fed mycelium extract in sugar syrup at 10% v/v). In each group of four cages, three cages were used for longevity tests and the remaining replicate cage was used for total viral particle testing. A separate experiment was conducted to evaluate the effect of fungal extracts on specific virus types.

Improvement in Longevity

For longevity (survivorship) testing, each replicate (three cages for each feeding concentration and control group) was monitored daily and dead bees were counted. For every day of the experiment, the total number of bees that died as of that date were tabulated for each replicate cage for each fungal extract and for the control groups. These daily dead bee tabulations were then used to calculate the percent of the original bees that were still surviving at each day of the experiment. The mean percent survival rates were then calculated based on the data from the three replicate cages for each fungal extract and for the control group.

Figure 2:
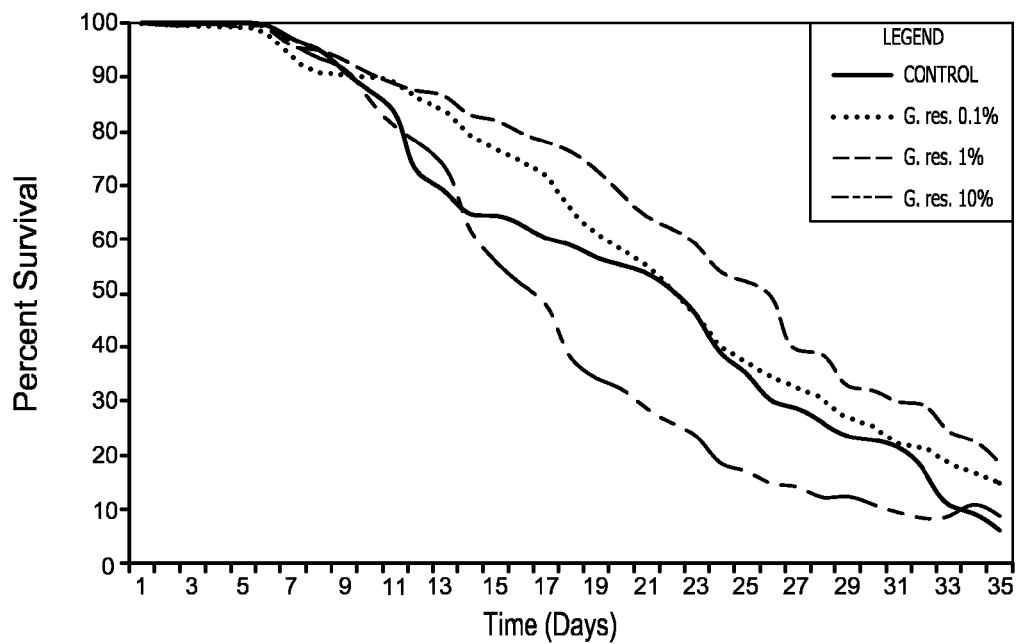
FIG. 2 is a line graph showing the percent survival of bees over time when given extracts of the mycelium of *Ganoderma resinaceum* (0.1%, 1% and 10%) with sugar water as compared to a control population fed sugar water only.
Figure 3:
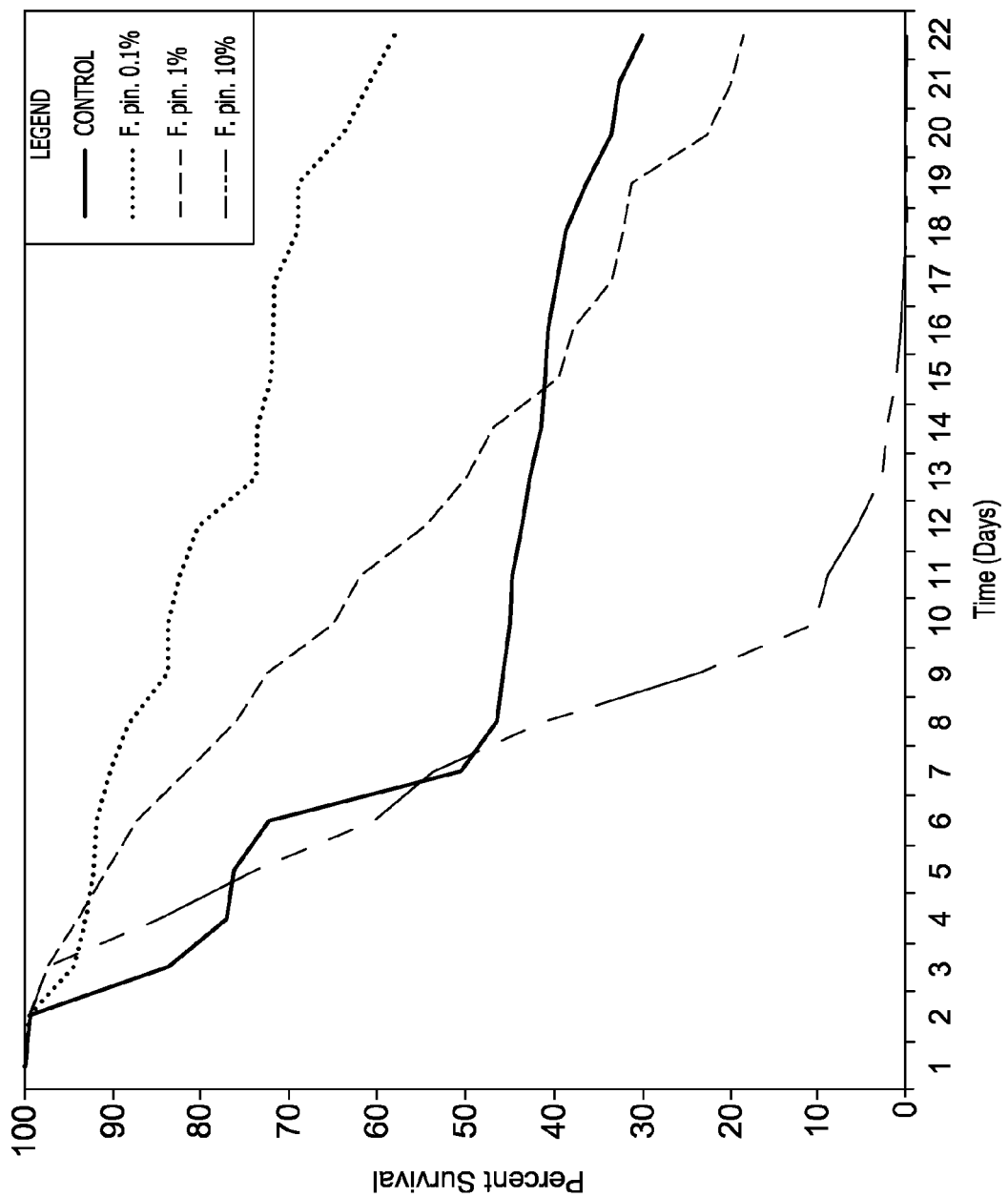
FIG. 3 is a line graph showing the percent survival of bees over time when given extracts of the mycelium of *Fomitopsis pinicola* (0.1%, 1% and 10%) with sugar water as compared to a control population fed sugar water only.
Figure 4:
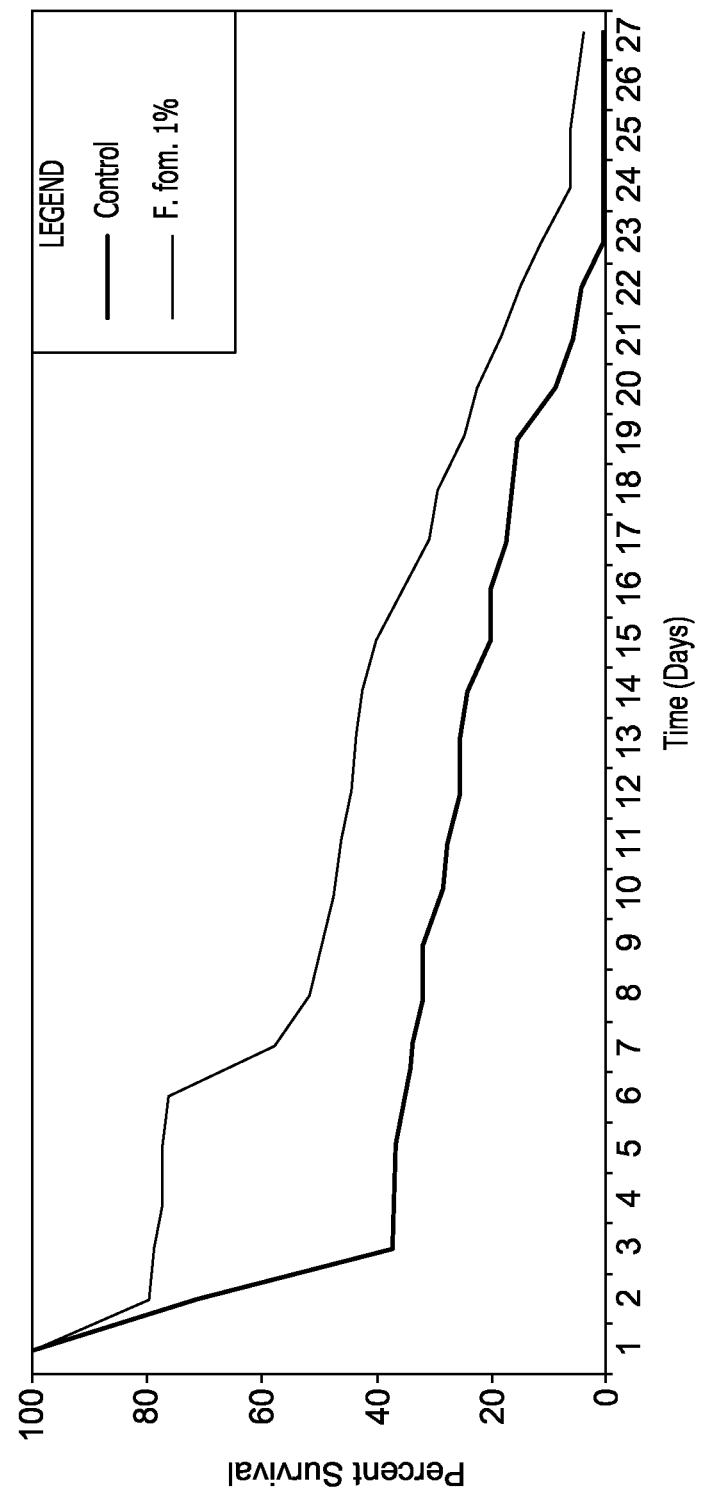
FIG. 4 is a line graph showing the percent survival of bees over time when given extracts of the mycelium of *Fomes fomentarius* (1%) with sugar water as compared to a control population fed sugar water only.

Survival plots were generated with time measured in days as the independent variable (x-axis), and the mean percent of bees surviving at any point in the experiment as the dependent variable (y-axis); the longevity graphs represent the % of the original population that is surviving at various points in time. See FIG. 1-4. FIG. 1 is a line graph showing percent survival of bees over time in days when given extracts of the mycelium of *Inonotus obliquus* (0.1%, 1% and 10% as respectively shown by dotted, dashed and double-dash lines) with sugar water as compared to a control population fed sugar water only (shown by a solid line). FIG. 2 is a line graph showing the percent survival of bees over time in days when given extracts of the mycelium of *Ganoderma resinaceum* (0.1%, 1% and 10% as respectively shown by dotted, dashed and double-dash lines) with sugar water as compared to a control population fed sugar water only (shown by a solid line). FIG. 3 is a line graph showing the percent survival of bees over time in days when given extracts of the mycelium of *Fomitopsis pinicola* (0.1%, 1% and 10% as respectively shown by dotted, dashed and double-dash lines) with sugar water as compared to a control population fed sugar water only (shown by a solid line). FIG. 4 is a line graph showing the percent survival of bees over time in days when given extracts of the mycelium of *Fomes fomentarius* (1% shown by a light solid line) with sugar water as compared to a control population fed sugar water only (shown by a dark solid line). These and similar approaches can be used in the practice of the invention to demonstrate the effect of the invention on the health and longevity of the bees. The figures are mean values of the experiments; the standard deviation bars were removed for clarity.

Figure 5:
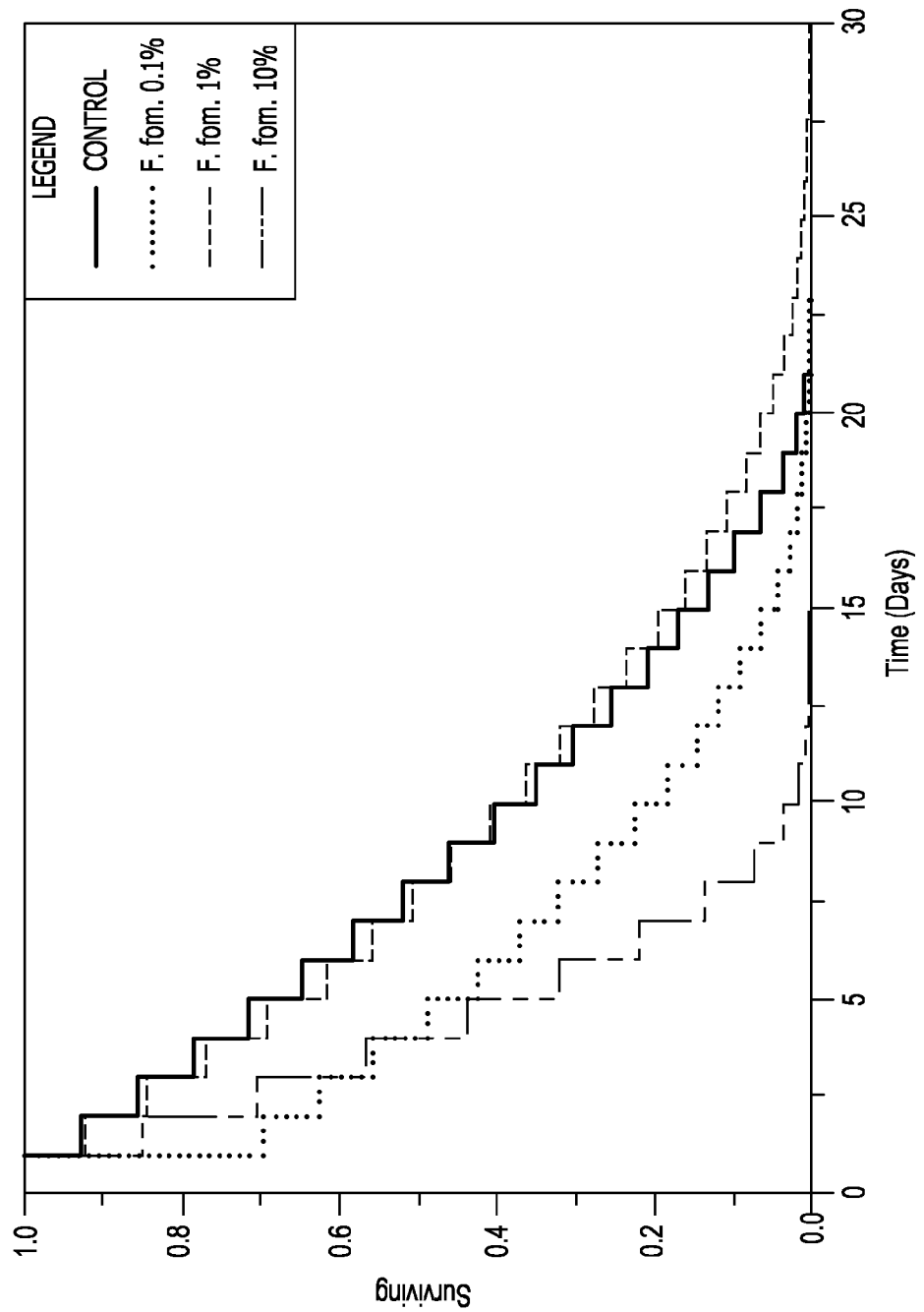
FIG. 5 is a graph of Kaplan-Meier (product-limit) survival estimates showing the fraction of bees surviving over time when given extracts of the mycelium of *Fomes fomentarius* (0.1%, 1% and 10%) with sugar water as compared to a control population fed sugar water only.

Some, but not all, of the results in these preliminary experiments were statistically significant; improved results are expected in continuing trials with more replicates. Statistical significance was assessed using Kaplan-Meier (product-limit) survival estimates prepared using JMP® statistical discovery software from SAS Institute, Inc. See FIG. 5, a graph of Kaplan-Meier (product-limit) survival estimates showing the fraction of bees surviving over time in days when given extracts of the mycelium of *Fomes fomentarius* (0.1%, 1% and 10% as respectively shown by dotted, dashed and double-dash lines) with sugar water as compared to a control population fed sugar water only (shown by a solid line). This analysis compared the mean survival time for the treatment to the mean survival time for the control (fed just sugar water) and used a Wilcoxon test to assess whether the survival was statistically different from chance variation in bee survival time. FIG. 5 illustrates this embodiment of the invention. In this analysis a composition of *Fomes fomentarius* fed at 1% v/v improved the mean survival of bees by 9.7% (p<0.0006).

As demonstrated in FIG. 1-5, longevity of bees fed extracts of different fungal species was improved, with improvement in longevity dependent on both the fungal species and the concentration consumed by the bees. In the practice of the current invention, some of this increase in longevity is probably due to a reduction in viral burden in most instances (as discussed below), but is also attributable to other aspects of the invention in the instance where longevity improved but viruses were not reduced.

Improvement in longevity can be demonstrated in the practice of the invention by the use of survival plots, such as but not limited to, those described above. Improvement in longevity can be measured numerically in the practice of the invention by calculating the difference in survival. One such method is based on the average value of a function theorem:

$$f_{avg} = \frac{1}{b-a}\int_a^b f(x)\,dx$$

Where values of 'a' and 'b' represent the starting and ending days over which the effect of the invention is being measured, and 'f(x)' represents the survival plot function as previously described. The difference in these figures over the specified time interval represents average percent improvement in longevity achieved through the practice of the invention over the specified time interval.

Other methods for measuring differences in longevity, survival, or population increases, including statistical methods such as Kaplan-Meyer analysis, Nelson Aalen and other methods for which are known to those skilled in the art are acceptable alternatives in the practice of the invention.

Similarly, various quantitative methods of assaying virus numbers in bees may be utilized in the practice of the present invention, including reverse transcription Polymerase Chain Reaction (RT-PCR) and real-time RT-PCR based on the PCR amplification of cDNA, ELISA (enzyme-linked immunosorbent assay), including both normal and sandwich ELISA with the various blocking agents, primary/secondary antibodies, reporter enzymes and their specific colorimetric substrate solutions for detection and quantification, multiplexing microarrays utilizing molecular probes for different target RNAs or DNAs, AGID (Agarose Gel Immuno-diffusion), serology methods based on protein profiles or polyclonal and monoclonal antibodies and the large variety of other molecular biology based methods such as high throughput sequencing technologies, pyrophosphate-based sequencing techniques, Sanger sequencing (also referred to as the chain termination method) and integrated virus detection systems (IVDS). See, for example, De Miranda, Diagnostic techniques for virus detection in honey bees, in Aubert et al. (Eds.), *Virology and the honey bee*, EEC Publications (2008), pp. 121-232 and Evans et al., Standard methodologies for molecular research in *Apis mellifera*, *Journal of Apicultural Research* 52(4) (2013).

Using this method for measuring the difference in longevity, the inventor specifies the improvement in longevity as embodied by this invention. See Table II, "Average Percent Improvement in Longevity of Bees." The table represents the difference between the average values of % of bees surviving, when assessed over various time intervals. That difference is given as the numerical subtraction of these percentages, with the average percent surviving over various time intervals calculated as previously described:

longevity improvement=avg % surviving$_{fed\ fungal\ extract}$-avg % surviving$_{control}$ Improved longevity increases the number of "bee days" in which workers or other classes of bees are available to gather pollen and maintain the hive or perform other labor, whereby the improved health and increased survival of the individuals leads to improved colony health and survival.
Reduction in Total Virus Level For antiviral testing of each type of mycelium extract (mushroom species), mixed aged honey bees from a single hive were collected on a single day and distributed at random into four cages of roughly 100 bees each. This trial was done in parallel to the longevity testing previously described, using bees from the same hives over the same time interval. Each fungal species set consisted of a control cage (fed sugar syrup), a low concentration cage (fed mycelium extract in sugar syrup at 0.1% v/v), a medium concentration cage (fed mycelium extract in sugar syrup at 1% v/v), and a high concentration cage (fed mycelium extract in sugar syrup at 10% v/v).

Samples of bees were removed from the cage and were frozen at day 0, day 7, and day 14. Assay of the total number of virus particles, irrespective of viral species, was carried out by Dr. David Wick of BVS, Inc. utilizing IVDS technology; see U.S. Pat. Nos. 8,524,155, 8,309,029, 8,146,446, 8,021,884, 7,850,908, 7,250,138, 6,491,872, 6,485,686 and 6,051,189 (all to Charles Wick) and Charles H. Wick, Integrated Virus Detection, CRC Press (2014). For each sample analysis, 6.0 grams of bees were blended with 100 ml of Reverse Osmosis (RO) water and coarse filtered through dual layer cheesecloth. A 90 ml sub-sample was then centrifuged for 60 minutes at 20,000×g. The supernatant was recovered and ultrafiltered through a 500,000 Dalton hollow fiber filtration system followed by a rinse with a 200 ml RO wash and reduction to approximately 2 ml. The solution was prepared for Integrated Virus Detection System (IVDS) analysis using a 1:10 dilution with Ammonium Acetate (AA). Each sample was filtered through a w-41 20 μm paper or a 0.45 μm PTFE filter. Samples were scanned five times with the IVDS and average virus levels were reported.

Figure 6:
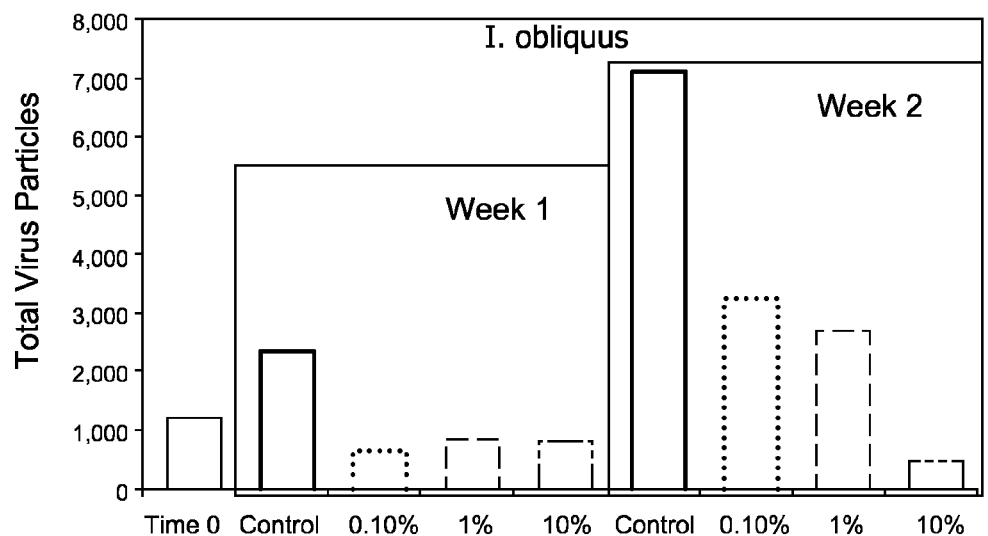
FIG. 6 is a bar graph showing total virus particles in a control population and bees given extracts of the mycelium of *Inonotus obliquus* (0.1%, 1% and 10%) with sugar water as compared to a control population fed sugar water only at time zero, one week and two weeks.
Figure 7:
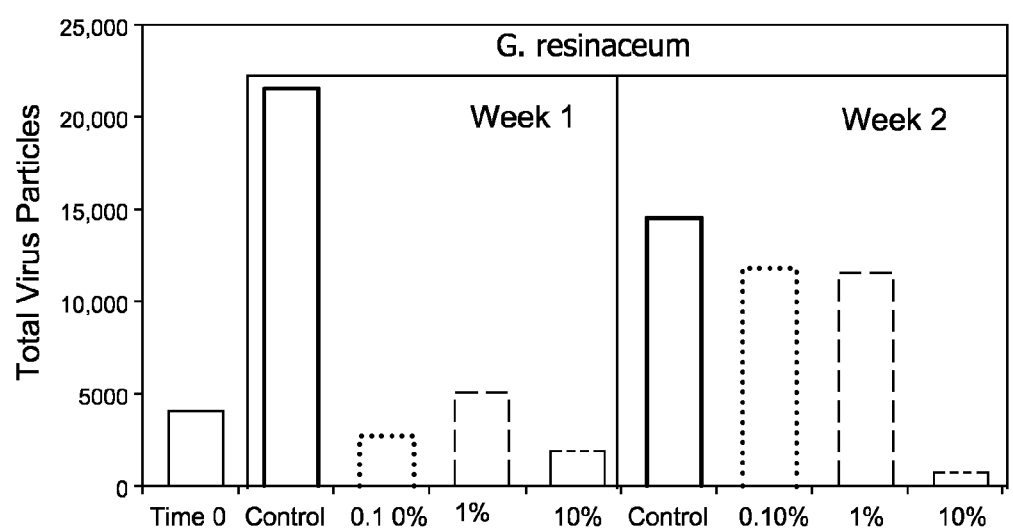
FIG. 7 is a bar graph showing total virus particles in a control population fed sugar water only and bees given extracts of the mycelium of *Ganoderma resinaceum* (0.1%, 1% and 10%) with sugar water as compared to a control population at time zero, one week and two weeks.
Figure 8:
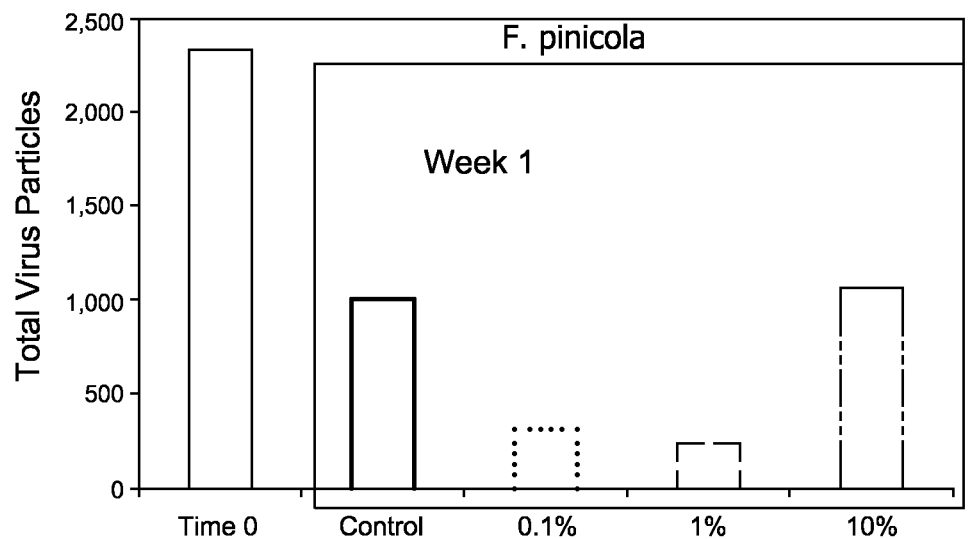
FIG. 8 is a bar graph showing total virus particles in bees given extracts of the mycelium of *Fomitopsis pinicola* (0.1%, 1% and 10%) with sugar water as compared to a control population fed sugar water only at time zero and one week.
Figure 9:
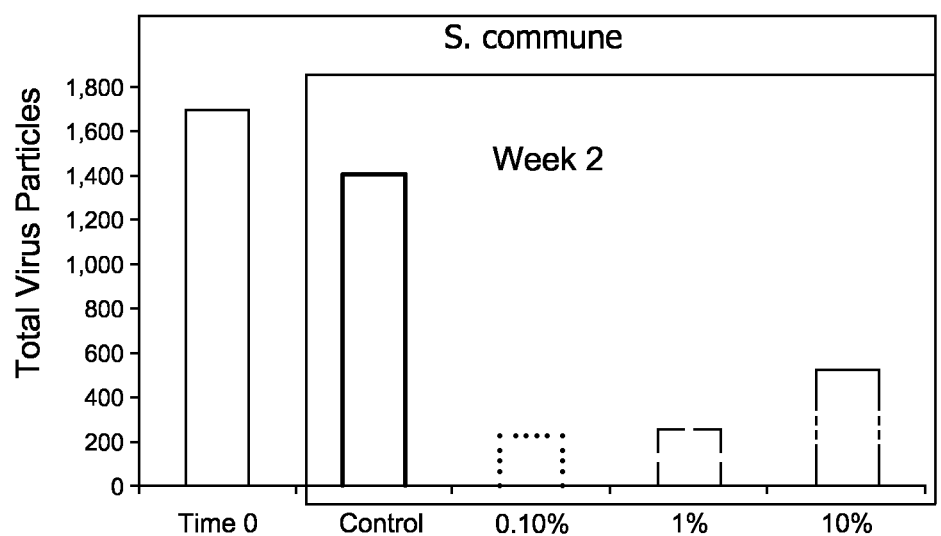
FIG. 9 is a bar graph showing total virus particles in and bees given extracts of the mycelium of *Schizophyllum commune* (0.1%, 1% and 10%) with sugar water as compared to a control population fed sugar water only at time zero and two weeks.

As demonstrated in FIGS. 6, 7, 8 and 9, the total viral load of bees fed extracts of different fungal species was reduced, with the level of virus reduction dependent on both the fungal species and the concentration consumed by the bees. FIG. 6 is a bar graph showing total virus particles in bees given extracts of the mycelium of *Inonotus obliquus* (0.1%, 1% and 10% as respectively shown by dotted, dashed and double-dash lines) with sugar water as compared to a control population fed sugar water only (shown by a solid line) at time zero, one week and two weeks. FIG. 7 is a bar graph showing total virus particles in bees given extracts of the mycelium of *Ganoderma resinaceum* (0.1%, 1% and 10% as respectively shown by dotted, dashed and double-dash lines) with sugar water as compared to a control population fed sugar water only (shown by a solid line) at time zero, one week and two weeks. FIG. 8 is a bar graph showing total virus particles in bees given extracts of the mycelium of *Fomitopsis pinicola* (0.1%, 1% and 10% as respectively shown by dotted, dashed and double-dash lines) with sugar water as compared to a control population fed sugar water only (shown by a solid line) at time zero and one week. FIG. 9 is a bar graph showing total virus particles in bees given extracts of the mycelium of *Schizophyllum commune* (0.1%, 1% and 10% as respectively shown by dotted, dashed and double-dash lines) with sugar water as compared to a control population fed sugar water only (shown by a solid line) at time zero and two weeks. These and similar figures can be used in the practice of the invention to demonstrate the effect of the invention on the health of the bees. In the practice of the current invention, most but not all, of the species that had improved longevity also had reduced virus load. This implies that viral reduction can help longevity, but that improvements in longevity may be seen without viral reduction because of other beneficial aspects of the invention such as general stimulation of hive immunity and antibiotic activity against non-viral pathogens like *Nosema*. Multiple causes of longevity improvement are likely in the practice of the invention because different fungal species appear have different and specific modes of action against different bee pathogens as disclosed below, by way of example and not exclusion.

Reduction in total viral load can be measured in the practice of the invention by calculating the difference in the virus detection between bees to which the invention has been applied and bees which have not been exposed to the invention. One such method for quantifying this difference is based on the average value of a function theorem:

$$f_{avg} = \frac{1}{b-a}\int_a^b f(x)\,dx$$

Where values of 'a' and 'b' represent the starting and ending days over which the effect of the invention is being measured, and 'f(x)' represents the virus detection level as a function of temporal sampling. The "percent difference" in these values over the specified time interval represents average "percent reduction" in virus level achieved through the practice of the invention over the specified time interval. Other methods for measuring differences virus level over time, including percent difference at individual sampling time points, mean difference, and statistical methods such as Kaplan-Meyer analysis are acceptable alternatives in the practice of the invention and are incorporated by reference. Using the method described above for measuring the difference in virus level over various time intervals, the inventor specifies the reduction in virus as embodied by this invention. See Table I, "Average Percent Decrease in Total Viral Burden."

The table represents the difference between the average values of % of bees surviving, when assessed over various time intervals. That difference is given not as the numerical subtraction of these percentages, but rather as the "percent reduction":

$$\% \text{ decrease in viral burden} = \frac{\text{avg virus titer}_{fed\ fungal\ extract} - \text{avg virus titer}_{control}}{\text{avg virus titer}_{control}} \times 100$$

Fungal Species/Disease Specificity

Specific types of mycelium extract (mushroom species), when fed to mixed aged bees can reduce the level of disease causing agents such as virus particles in a species-specific way. This embodiment of the invention was demonstrated by feeding fungal extracts to caged bees and measuring the levels of specific types of virus in the bees over time. For this analysis, mixed aged bees from a single hive were collected on a single day and were evenly distributed at random into 12 cages. Four cages were fed *Ganoderma lucidum* var. *resinaceum* mycelium extract at 1% v/v in sugar syrup, four cages were fed *Inonotus obliquus* mycelium extract at 1% v/v in sugar syrup, and four were used as a control and were fed only sugar syrup.

Samples of bees were removed from the cage and were frozen at day 0, day 3, day 7 and day 14. Bees were sent to Dr. Yanping (Judy) Chen of the United States Department of Agriculture—Agricultural Research Service using real time RT-PCR as described in Chen et al., Quantitative real-time reverse transcription-PCR analysis of Deformed Wing Virus infection in the honeybee (*Apis mellifera* L.), *Appl. Environ. Microbiol.*, Vol. 71 (2005), p. 436-441 and Khongphinitbunjong et al., Differential viral levels and immune gene expression in three stocks of *Apis mellifera* induced by different numbers of *Varroa destructor, Journal of Insect Physiology*, Vol. 72 (2015), p. 28-34.

Figure 10:
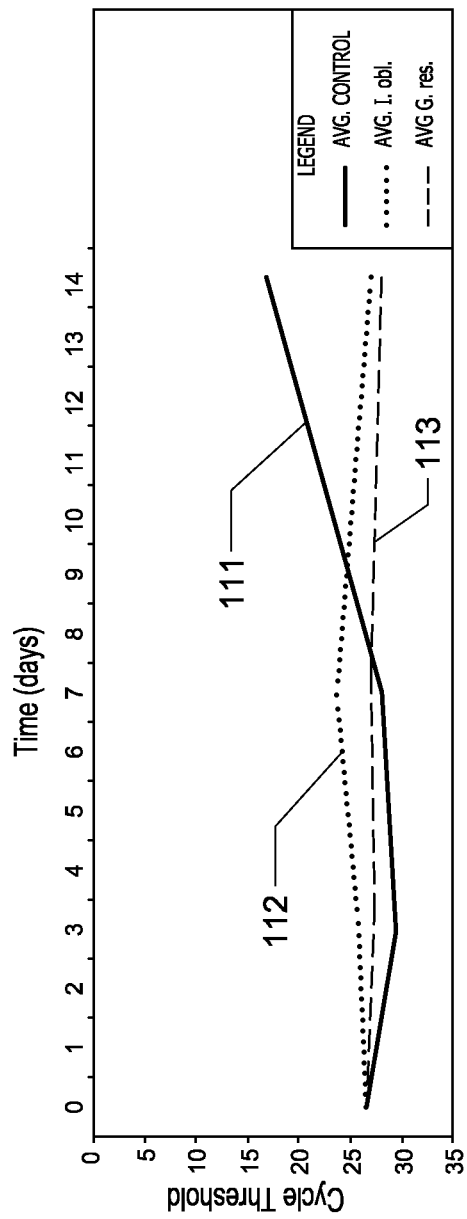
FIG. 10 is a line graph showing cycle threshold for Black Queen Cell Virus over time in a control population and bees given extracts of the mycelium of *Inonotus obliquus* (1%) and *Ganoderma resinaceum* (1%) with sugar water as compared to a control population fed sugar water only.
Figure 11:
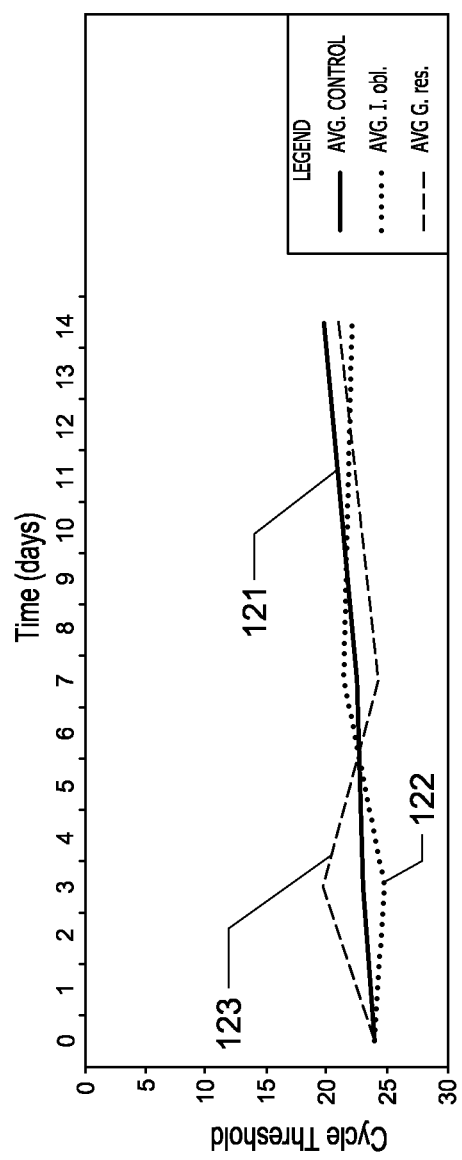
FIG. 11 is a line graph showing cycle threshold for Deformed Wing Virus over time in a control population and bees given extracts of the mycelium of *Inonotus obliquus* (1%) and *Ganoderma resinaceum* (1%) with sugar water as compared to a control population fed sugar water only.

In this analysis, levels of virus are quantified based on the accumulation of a fluorescent signal as DNA of the virus is amplified in the PCR reaction. The cycle threshold is defined as the number of cycles required for the fluorescent signal to exceed the fluorescence background level. Cycle threshold levels are therefore inversely proportional to the amount of target viral nucleic acid (e.g., virus titer) in the sample (i.e. the lower the CT level the greater the amount of target nucleic acid in the sample). As demonstrated in FIG. 10, the levels of Black Queen Cell Virus (as quantified based on cycle threshold) were prevented from increasing in bees that were fed extracts of *Ganoderma lucidum* var. *resinaceum* and *Inonotus obliquus* mycelium. See FIG. 10, a line graph showing cycle threshold for Black Queen Cell Virus over time in a control population fed sugar water only (shown by solid line 111) as compared to bees given extracts of the mycelium of *Inonotus obliquus* (1%) (shown by dotted line 112) and *Ganoderma resinaceum* (1%) (shown by dashed line 113) with sugar water. By contrast, the same extracts did not have a significant effect on levels of Deformed Wing Virus. See FIG. 11, a line graph showing cycle threshold for Deformed Wing Virus over time in a control population fed sugar water only (shown by solid line 121) and bees given extracts of the mycelium of *Inonotus obliquus* (1%) (shown by dotted line 122) and *Ganoderma resinaceum* (1%) (shown by dashed line 113) with sugar water.

This example of a fungal species extract having specificity against one viral pathogen and not against another embodies the antiviral invention. It also supports the argument that specific compositions of fungal extracts can be similarly specific to other bee pathogens (that reduce longevity) such as *Nosema* and bacteria and/or can, in general, up-regulate metabolic, immune and detoxification systems of bees. Such effects against non-viral pathogens or general metabolic and immunity boosts may have been responsible for the instances where longevity was improved but viral load remained unchanged.

Summary, Preferences, and Implications

To date, the inventor has data (both a longevity experiment and a total virus reduction experiment) for 8 species of medicinal mushrooms. The inventor also has a third experiment, reduction of a specific virus, Black Queen Cell virus, done only on *Ganoderma resinaceum* and *Inonotus obliquus*.

The inventor herein defines a metric, the "LV index", which is: LV Index=The average percent improvement in bee longevity multiplied by the average percent decrease in total viral burden.

This computation gives a number that assigns equal importance to both aspects for measuring improvement to colony health. Blank boxes in the tables below for antiviral activity, longevity or LV indicate that either longevity or virus reduction was negative or zero in one or both data sets.

There are many other possible mathematical representations that could draw a relationship between these data sets, such as, for example, percent longevity improvement divided by percent virus reduction. That calculation would stress the portion of the longevity that could theoretically be related to virus reduction if there were a 1:1 correspondence between these measures. Numerous possibilities for a metric will be apparent to those skilled in the arts and all such metrics for improved bee health should be considered to be within the scope of the invention.

The general approach adopted herein is to compare the "area under the curve" of longevity measurements and total virus reduction measurements as previously described. The difference between the areas under the curves, over a given time interval, is equal to the numbers in the longevity table. The difference in the area under the curves, over a given time interval, expressed as a "percent improvement" is equal to the numbers in the total virus reduction tables. See Table I "Average Percent Decrease in Total Viral Burden" and Table II "Average Percent Improvement in Longevity of Bees". These values can then be related mathematically to illustrate features of interest in the practice of the invention such as compositions that are most preferred for improving longevity and reducing total viral load in bees. See Table III Average Percent Improvement in Longevity of Bees×Average Percent Decrease in Total Viral Burden (LV Index).

TABLE I

Average Percent Decrease in Total Viral Burden

| Species | Timeframe | Concentration | | |
| --- | --- | --- | --- | --- |
| | | 0.1% | 1% | 10% |
| Trametes versicolor | 0-7 days | 7.5 | | 9.0 |
| | 0-14 days | 4.8 | | 3.6 |
| Fomitopsis pinicola | 0-7 days | 20.4 | 22.8 | |
| | 0-14 days | 25.5 | 32.2 | 2.1 |
| Fomitopsis officinalis | 0-7 days | | | |
| | 0-14 days | 4.5 | | |
| Schizophyllum commune | 0-7 days | | | 3.8 |
| | 0-14 days | 19.5 | 20.8 | 26.7 |
| Inonotus obliquus | 0-7 days | 47.5 | 41.6 | 42.2 |
| | 0-14 days | | | |
| Fomes fomentarius | 0-7 days | 9.6 | | 10.0 |
| | 0-14 days | 9.3 | | |
| Ganoderma applanatum | 0-7 days | 2.5 | 3.6 | 1.0 |
| | 0-14 days | 4.5 | 14.2 | |
| Ganoderma lucidum var. resinaceum | 0-7 days | 73.4 | 64.4 | 76.7 |
| | 0-14 days | 65.4 | 58.3 | 85.9 |

TABLE I-continued

Average Percent Decrease in Total Viral Burden

| Species | Timeframe | Concentration | | |
| --- | --- | --- | --- | --- |
| | | 0.1% | 1% | 10% |
| Preferred | 1-25% or greater decrease in virus | | | |
| More Preferred | 15-25% or greater decrease in virus | | | |
| Most Preferred | >25% decrease in virus | | | |

TABLE II

Average Percent Improvement in Longevity of Bees

| Species | Timeframe | Concentration | | |
| --- | --- | --- | --- | --- |
| | | 0.1% | 1% | 10% |
| Trametes versicolor | 0-7 days | 4.1 | 0.2 | 5.0 |
| | 0-14 days | 3.8 | | 7.8 |
| | 0-28 days | 1.6 | | 3.7 |
| Fomitopsis pinicola | 0-7 days | 9.2 | 14.6 | |
| | 0-14 days | 13.5 | 14.1 | |
| | 0-28 days | 8.5 | 3.7 | |
| Fomitopsis officinalis | 0-7 days | 5.2 | 3.8 | |
| | 0-14 days | 2.3 | 1.0 | |
| | 0-28 days | 1.0 | | |
| Schizophyllum commune | 0-7 days | 0.1 | | 0.8 |
| | 0-14 days | 3.7 | 0.5 | |
| | 0-28 days | 0.1 | | |
| Inonotus obliquus | 0-7 days | | 1.6 | 1.2 |
| | 0-14 days | | 4.1 | 2.1 |
| | 0-28 days | | | 3.7 |
| Fomes fomentarius | 0-7 days | 1.7 | 22.1 | 13.5 |
| | 0-14 days | | 16.1 | |
| | 0-28 days | | 11.2 | |
| Ganoderma lucidum var. resinaceum | 0-7 days | | | |
| | 0-14 days | | 2.2 | 3.7 |
| | 0-28 days | | 3.7 | 9.5 |
| Preferred | 1-5% or greater improvement in longevity | | | |
| More Preferred | 3-5% or greater improvement in longevity | | | |
| Most Preferred | >5% improvement in longevity | | | |

TABLE III

Average Percent Improvement in Longevity of Bees ×
Average Percent Decrease in Total Viral Burden (LV Index)

| Species | Timeframe | Concentration | | |
| --- | --- | --- | --- | --- |
| | | 0.1% | 1% | 10% |
| Trametes versicolor | 0-7 days | 30.9 | | 44.8 |
| | 0-14 days | 18.1 | | 27.7 |
| Fomitopsis pinicola | 0-7 days | 187.5 | 332.7 | |
| | 0-14 days | 344.1 | 453.1 | |
| Fomitopsis officinalis | 0-7 days | | | |
| | 0-14 days | 10.4 | | |
| Schizophyllum commune | 0-7 days | | | 3.1 |
| | 0-14 days | 72.6 | 9.6 | |
| Inonotus obliquus | 0-7 days | | 67.0 | 51.2 |
| | 0-14 days | | | |
| Fomes fomentarius | 0-7 days | 16.2 | | 135.2 |
| | 0-14 days | | | |
| Ganoderma applanatum | 0-7 days | | | |
| | 0-14 days | | | |
| Ganoderma lucidum var. resinaceum | 0-7 days | | | |
| | 0-14 days | 147.1 | 212.9 | |
| Preferred | 1-200+ LV index | | | |
| More Preferred | 50-200+ LV index | | | |
| Most Preferred | 200+ LV index | | | |

In the practice of the invention, fungal extract compositions may be variously ranked with regard to preference depending on the intended application of the composition.

Examples include but are not limited to ranking with preference to longevity improvement, ranking with preference to total virus reduction, ranking with regard to longevity and virus reduction. Notably, preference may also be given to compositions which improve longevity but do not reduce viruses. Such compositions are expected to improve longevity by acting on bee stressors that are unrelated to viruses (examples include *Nosema* infection, pesticide exposure, stress from cold temperatures, etc.).

Example 7

*Ganoderma resinaceum* extract at 14 days resulted in an almost 20% increase in survival of worker bees over the controls. See also FIG. 5. This differential can be hugely significant in helping the colony survive as the longevity of worker bees during this critical time results in nurse bees not being prematurely recruited, thus allowing them to better attend to keeping the brood, the next generation, healthy. The addition of mycelial extracts from *Ganoderma resinaceum* resulted in a dramatic reduction in overall viral pathogen payloads in bees (from multiple viruses), while the sugar control, without mycelial extracts, resulted in increased population of overall viruses. As viruses are thought by many bee entomologists to be the most significant disease challenge, often facilitating the subsequent infection from other bacterial (i.e. foulbrood) and fungal species, reducing viruses can be a keystone advantage in protecting bees from colony collapse disorders and their many associated stressors.

In terms of increasing longevity, the addition of 1% mycelial extracts of *Fomes fomentarius* and *Ganoderma resinaceum* to sugar water (water-50 grams, sugar 49.5 grams, mycelial extract 0.5 grams), statistically, significantly extended the lifespans of bees—in terms of 'bee days of life' by 17.6% and 8.9%, respectively. Extended average lifespan results in more workers being available for job tasks, a significant advantage to stressed bee colonies on very thin operating margins and stressed colonies on the edge of collapse. When there are more bees at any one time that is significant for pollen acquisition and hive maintenance. By extension, many more hives can be saved feeding them mycelial extracts in their sugar water over those just having sugar water without mycelial extracts. Until we do field trials, we do not know yet how many more bee days will tilt the balance to help bees overcome CCD since there are so many complexities. However, the consensus amongst bee scientists is that increasing longevity of worker bees, under stress, is a strong advantage. Moreover, when the extracts are made from, in these cases, birch tree wood (*Betula* species), the same tree species these polypore mushrooms habit, and ones in which bees nest, the extracts may become more potent while less expensive to produce. That we can show such strong, significant activity from mycelium grown on rice strengthens the argument that the mycelium is the causal benefitting factor (the rice controls showed no activity.) By utilizing mycelium grown on rice as spawn to inoculate 10-100× more mass in the form of birch sawdust expands the mycelium exponentially over the mycelium-on-rice extracts reported here. The mycelium grows more densely branched and compacted mycelial networks on birch sawdust compared to rice, meaning more surface areas is generated for the expression of extracellular constituents. Hence, this inventor anticipates mycelial extracts from birch sawdust will be a preferred embodiment of this invention.

Many *Ganoderma* and other polypore species are anticipated to also offer a similar bioshield' of protection. No doubt, there will be gilled mushrooms, due to their close evolutionary relationship to polypores, to be of benefit similarly.

Example 8

A liquid extract of the mycelium, or a precipitate from such extract, or a concentrated extract from which all or part of the solvent has been removed, containing these active principles can be added to the honey, to honey-enriched water, to sugar water or bee candy, to pollen, to pollen substitutes, or to other substances in other manners obvious to those skilled in the art of apiary science or commercial practices. The extract can be used as an adjunct to other remedies making them more effective. The extracts can be in liquid, frozen, freeze dried, air dried, vacuum desiccated, refractance window dehydrated, sonically dehydrated, or partially purified forms, in amounts sufficient to have the effect of attracting bees and/or benefitting bee health, honey production and pollinations. Moreover, these derivative forms of extracts will be useful for human consumption as they are palatable, high in antioxidants, and in other properties beneficial to people, other animals, which includes bees.

Example 9

A preferred delivery system would be to incorporate the mycelial extracts into pollen patties or grease patties. Pollen patties are made by beekeepers and placed above the brood chamber as a source of nutrition. They can be made from a wide range of materials, including soy, brewer's yeast, sugar syrup and may optionally include organically grown pollen. These pollen patties supplement the bees nutritionally. Because they are widely used in the fall, they help the bees survive into the next year. These extracts also contain digestive enzymes which help the bees better metabolize food stocks, and help break down toxins and improve baseline immunity.

Example 10

A mixture of compositions comprising extracts of *Stropharia rugoso-annulata, Fomes fomentarius, Fomitopsis officinalis, Fomitopsis pinicola, Ganoderma resinaceum, Inonotus obliquus, Piptoporus betulinus, Trametes versicolor* and/or *Schizophyllum commune*, which together offer a plurality of benefits, can be added to water. The *Stropharia rugoso-annulata* attracts bees, has a flower-like fragrance, and provides sugar-rich (up to 75 polysaccharides) nutrient source. The *Fomes fomentarius* and *Fomitopsis officinalis* extracts confer antiviral benefits, plus those additional benefits already mentioned for *Stropharia rugoso-annulata*. All three extracts contain polyphenols, and more particularly coumarins, which help activate p450 enzyme pathways, which help bees detoxify endogenous, natural, foreign and anthropogenic toxins and their associated deleterious effects. A mixture of these extracts can be given to the bees via their drinking water, their enriched water, honey, propolis, pollen patties or even in the wax used for making preformed combs in the creation of supers for honey production.

Example 11

Add the extracts from the mycelium of *Fomitopsis officinalis, Fomitopsis pinicola, Fomes fomentarius, Inonotus obliquus, Schizophyllum commune, Ganoderma resina-*

*ceum, Piptoporus betulinus, Trametes versicolor* and/or *Inonotus obliquus* to the sugar-water typically fed to bees in the early spring before pollen levels rise, to help reduce resident viral loads early in the season, preventing their escalation to the level of becoming a behavior-altering disease or for causing bee-to-bee transfer of pathogens. The extracts can simply be mixed into the sugar water at a rate sufficient to have a positive effect. The range could preferably be 0.01-20%, or more preferably 0.1-10% of the volume of the sugar water compositions employed by beekeepers. The extracts would be mixed in the water first and then added to the sugar to make the typical syrup. The high sugar content would act as a preservative to keep the antiviral and antibacterial properties long lasting.

Example 12

Extracts of medicinal mushroom mycelium can be soaked into paper strips. These paper strips can be combined with an adhesive. The low pH of the many medicinal mushroom mycelium extracts, in the pH 0.5-4 range, is toxic to mites but harmless to bees upon contact. Oxalic acid solution may optionally be added in effective amounts.

Example 13

Use extracts of the mycelium or fruitbodies from *Ganoderma lucidum, Ganoderma resinaceum, Fomitopsis pinicola, Fomitopsis officinalis, Inonotus obliquus, Piptoporus betulinus, Trametes versicolor* and *Schizophyllum commune* whereby the extracts are concentrated into a form attractive to bees and sufficient, upon contact, to have the effect of reducing the Tobacco Ringspot Virus, the Israeli Acute Paralysis Virus, the Black Queen Cell Virus, the Invertebrate Iridescent Virus, or IIV6, and *Nosema* microsporidia, resulting in bees being able to better overcome colony collapse disorder.

Example 14

Use extracts of the mycelium or fruitbodies from *Ganoderma lucidum, Ganoderma resinaceum, Fomes fomentarius, Fomitopsis pinicola, Fomitopsis officinalis, Schizophyllum commune, Inonotus obliquus* and *Stropharia rugoso-annulata* whereby the extracts are concentrated into a form that resembles the texture and consistency of honey, in a form attractive to bees and sufficient, upon contact, to have the effect of reducing viruses, including but not limited to the Tobacco Ringspot Virus, the Israeli Acute Paralysis Virus, the Black Queen Cell Virus, and *Nosema* microsporidia, and causing the up-regulation of cytochrome p450 enzyme pathways, improving overall immune function, foraging ability, overwintering, drought resistance, ability to overcome losses of nectar providing plants, resulting in an improved health to bees so that there is a measurable benefit for beehives to survive and overcome CCD and produce descendent generations. This "mycological honey" can be used separately, or mixed into bee honey to attract and benefit bees. Moreover, this "mycological honey" can be partially dissolved into water as a foliar spray to plants or applied directly onto bees. Additionally, this 'mycological honey' can be marketed as a nutraceutical for human consumption.

Example 15

Bees flying to or from the sugar water, upon entering the beehive, buzz and shake their bodies to dislodge the mites. If the mites fall through a screen, they are in contact with or attracted to the entomopathogenic mycoattractant, which in itself may be lethal, or onto insecticidal mycelium, wherein the mites sicken or die, reducing the mites' ability to travel and infect, thus lessening its threat vector to bees. Moreover, if bees are sprayed with an oxalic acid enriched spray, the parasitic mites become more susceptible to the infectious or lethal properties of the entomopathogenic fungi.

Example 16

The extracts, hyphal fragments or spores of beneficial fungi, such as *Stropharia rugoso-annulata*, and the spores of entomopathogenic fungi such as Entomophthorales, can be incorporated as a mixture into the extract-enriched sugar water, bee foods or honey, which allows for transference into the honey production stream, benefitting the brood, the drones, the queen and the hive overall.

Example 17

Extracts of the mycelium of, or spores, hyphal fragments, or tissue of, *Stropharia rugoso-annulata* can be presented on paper strips or in water accessible to the bees. The fragrance of *Stropharia rugoso-annulata*, to which bees can be accustomed, helps foraging bees to return to their colonies if these fragrances are placed near to or within the hives. Such fragrances can be emitted via any method known to the art of delivery of fragrances, foggers, sprays or aerosol dispensers. It is expected that the extracts of *Stropharia* rugoso-*annulata* mycelium and the extracts of other mushroom mycelia will induce trail following or navigation behavior via "dance language" and odor plumes.

Example 18

Spores and hyphae of *Metarhizium anisopliae* may be mixed with the mycelium *Fomes fomentarius* for producing anti-*Varroa* mite sprays and smokes for helping bees resist mites, viruses, etc. for overcoming CCD. Many strains of *Metarhizium* are relatively nontoxic; "No harm is expected to humans from exposure to *Metarhizium anisopliae* strain F52 by ingesting, inhaling, or touching products containing this active ingredient." *Metarhizium anisopliae* strain F52 (029056) Biopesticide Fact Sheet.

Example 19

A mixture of compositions of extracts of *Stropharia rugoso-annulata, Fomitopsis officinalis, Fomitopsis pinicola, Fomes fomentarius, Ganoderma resinaceum, Inonotus obliquus, Piptoporus betulinus, Trametes versicolor* and/or *Schizophyllum commune* and *Metarhizium anisopliae*, which together offer a plurality of benefits, can be added to water. The *Stropharia rugoso-annulata* attracts bees, has a flower-like fragrance, and provides sugar rich (up to 75 polysaccharides) nutrient source. The various extracts confer antiviral and antibacterial benefits and life extension, plus the attractancy of *Stropharia* rugoso-*annulata*. The *Metarhizium anisopliae* extracts can be presented in sticky strips or mats, or into any sticky, mite- or Phorid fly-capturing substance, or in water accessible to the same to attract mites and Phorid flies, whereupon contact, they are debilitated or killed, reducing their ability to be a vector of disease; *Varroa* mite populations can be reduced using *Metarhizium anisopliae* extracts before the brood chambers are sealed, reducing bee deaths from exposure to mites and the diseases they carry. All three extracts contain polyphenols, and more particularly coumarins, which help activate p450 enzyme pathways, which help bees detoxify endogenous, foreign, natural and anthropogenic toxins and lessen their associated deleterious effects. A solution of these mixed extracts can be given to the bees via nectar feeders containing their drinking water or their sugar or fructose enriched water, via mixing into bee candy, honey, propolis, pollen patties or even by mixing into the wax used for making preformed combs in the creation of supers for honey production.

Example 20

Extracts of the preconidial mycelium of *Metarhizium anisopliae* pathogenic to mites and/or flies can be mixed with spores or hyphal fragments of same, and presented in sticky strips or mats, or into any sticky, mite- or Phorid fly-capturing substance, or in water accessible to the mites. This combination attracts mites or flies, which upon contact, infects them with an entomopathogenic fungus or exposes them to a lethal doses of entomopathogenic toxins.

Example 21

Extracts of the preconidial mycelium of *Metarhizium anisopliae* mixed with the extracts, spores or hyphal fragments of *Stropharia rugoso-annulata* can be presented on paper strips or in water accessible to the bees. This combination attracts mites or flies, and bees, which upon contact harms the mites and flies but not bees.

Example 22

Extracts of the preconidial mycelium of *Aspergillus flavus, Aspergillus niger* and *Aspergillus fumigatus* can be mixed with the spores or hyphal fragments of *Stropharia rugoso-annulata* and presented on paper strips or in water accessible to the bees. This combination attracts mites or flies, and bees, which upon contact harms the mites and flies but not bees. Optionally, strains of *Aspergillus flavus, Aspergillus niger* and *Aspergillus fumigatus* can be used which have reduced aflatoxin and neurotoxin levels, below the levels which would harm bees but above the levels harming mites and flies, thus conferring a net benefit to bee colony health.

Example 23

Extracts of the preconidial mycelium of *Metarhizium anisopliae* can be mixed with the spores or hyphal fragments of *Stropharia rugoso-annulata* can be presented on paper strips or in water accessible to the bees. This combination attracts mites or flies, and bees, which upon contact harms the mites and flies but not bees. Optionally, strains of *Metarhizium anisopliae* can be used which have reduced destructin levels, below the levels which would harm bees but above the levels harming mites and flies, thus conferring a net benefit to bee colony health.

Example 24

Extracts of mushroom mycelium and/or extracts of the preconidial mycelium of *Metarhizium anisopliae* can be mixed with extracts or derivatives from Neem trees and presented on paper strips, in water accessible to the bees or in topical sprays. This combination attracts mites or flies, and bees, which upon contact harms the mites and flies but not bees. Optionally, strains of *Metarhizium anisopliae* can be used which have reduced destructin levels, below the levels which would harm bees but above the levels harming mites and flies, thus conferring a net benefit to bee colony health. Optionally, the concentration of Neem tree extracts (or the active ingredient azadirachtin), and sugars can be balanced to optimize benefits to bees by reducing mites and their foraging abilities, and their pathogen payloads. Furthermore, this combination can be further enhanced with the addition of extracts of Basidiomycetes fungi from agaricoid and polyporoid fungi, which not only provide mite-destroying oxalic acids, and toxin degrading enzymes, but also up-regulates bee's innate cytochrome p450 enzymatic pathways to break down anthropomorphic toxins, and additionally reduces virally, bacterially, and fungally associated pathogens afflicting bees. Such synergistic effects from multiple constituents have the net effect of helping bees better survive colony collapse disorder. A combination of using preconidial mycelium of *Metarhizium anisopliae*, the extracts of *Fomitopsis officinalis* and *Fomitopsis pinicola*, the extracts from Neem trees, the extracts of *Ganoderma lucidum, Ganoderma resinaceum, Ganoderma applanatum, Pleurotus ostreatus, Trametes versicolor* and *Stropharia rugoso-annulata* immersed and mixed into water is anticipated to be an effective composition and method for making a deliverable, efficacious bee spray or ingredient in pollen patties or drinking water. Similar compositions may be sprayed on plants or trees which bees pollinate, benefitting both plant and bee.

Example 25

The methods and compositions of oxalic acid, sugar (or polysaccharide) enriched water, and the preconidial hyphal fragments from *Metarhizium anisopliae* which upon contact with bees selectively harms the mites while having a net benefit to bees. This composition may optionally be combined with extracts of medicinal mushroom mycelium with antiviral and longevity enhancing properties and incorporated into bee food.

Example 26

The combination of the extracts from *Fomes fomentarius, Fomitopsis pinicola, Fomitopsis officinalis, Ganoderma lucidum, Ganoderma applanatum, Ganoderma resinaceum, Schizophyllum commune, Stropharia rugoso-annulata* and *Ganoderma resinaceum* in combination with the extracts of the preconidial mycelium of *Metarhizium anisopliae* to attract bees and mites whereby contact with this combination harms *Varroa* mites, reducing viruses, pathogenic fungi and bacteria, providing a net benefit for bees overcoming colony collapse disorder.

Example 27

The combination of the preconidial mycelium of *Metarhizium anisopliae* with polysaccharides of *Fomitopsis pinicola, Fomitopsis officinalis Ganoderma resinaceum, Ganoderma lucidum, Inonotus obliquus* and *Schizophyllum communes*, to attract bees and mites whereby contact with this combination harms *Varroa* mites, and reduces viruses, bacteriophages, pathogenic fungi and bacteria that harm bees but has a net benefit for bees overcoming colony collapse disorder.

Example 28

Use extracts of the mycelium or fruitbodies lacking melanin such as from so called albino fruitbodies of *Agaricus blazei, Fomitopsis officinalis, Fomitopsis pinicola, Fomes fomentarius, Schizophyllum commune, Trametes elegans* and *Stropharia rugoso-annulata* whereby the extracts are concentrated into a form that resembles the texture and consistency of honey, in a form attractive to bees and sufficient, upon contact, to have the effect of reducing the Tobacco Ringspot Virus, the Israeli Acute Paralysis Virus, Invertebrate Iridescent Virus, or IIV6, and *Nosema* microsporidia, and causing the up-regulation of cytochrome p450 enzyme pathways, improving overall immune function, foraging ability, overwintering, drought resistance, ability to overcome losses of nectar providing plants, resulting in an improved health to bees so that there is a measurable benefit for beehives to survive and overcome colony collapse disorder and produce descendent generations. This "mycological honey" can be used separately, or mixed into bee honey to attract and benefit bees. Moreover, this "mycological honey" can be partially dissolved into water as a foliar spray to plants or applied directly onto bees. Additionally, this 'mycological honey' can be marketed as a nutraceutical for human consumption.

Example 29

Culture the medicinal mushroom mycelium on plant materials which have activity against viruses, including *Ficus bengalensis* (Vad), *Ficus religiosa* (Pimpal), *Jasminum auriculatur* (Jaai), *Acacia catechu* (Khair), *Azadirachta indica* (Neem), *Curcuma longa* (Turmeric), *Withania somnifera* (Ashwagandha) and *Silybum marianum* (Milk Thistle). See Deshpande et al., Antiviral activity of plant extracts against sac brood virus in vitro—a preliminary report, *International Journal of Institutional Pharmacy and Life Sciences* 3(6): November-December 2013, p. 1-22.

Example 30

Fungally Treated Structural Materials to Help Protect Bee Colonies

Beehives are typically made of wood fibers, and stackable 'supers' hold frames upon which bees create honeycombs rich in honey, above the brood boxes. These supers and the other wood based frameworks used by beekeepers eventually degrade, often times growing molds that can be pathogenic to bees and encourage invasion by insects and arthropods. As a result, beekeepers typically replace their supers, brood boxes, and floors etc. every few years. The bases of bee hives tend to last longer, but ultimately all beehive boxes degrade with opportunistic, often pathogenic fungi, and the health of bee colonies can be negatively impacted as a result.

This invention is to add, incorporate, impregnate, coat, infuse or attach spores or fragments of mycelium, or extracts thereof, of beneficial fungi, more specifically mushroom forming fungi in the Class Basidiomycetes/Basidiomycota or Ascomycetes, into the frameworks of beehives, which impart a benefit to bee health by providing a host defense shield of singular or synergistic benefits. For instance, and not by limitation, the frames of supers can be made of sheets of wood, wood fiber, and a wide range agricultural products than be bound together with mycelium, with or without spores. Such fungally impregnated panels not only provide a structural benefit, but the fungi can have antiviral, antimiticidal, antibacterial, antifungal, anti-insecticidal properties that help bees dwelling on and within the materials used for building bee hives.

In addition to beehives, all structures that house animals may be advantageously treated with extracts or mycelium, including bird cages, barns and structures to house bats.

The materials that can be used to host these beneficial fungi can be made of wood, particle boards, biodegradable structured panels, fungally grown wood panel substitutes, non-biodegradable materials, and may also be incorporated into the bees wax used for the frames, or even the propolis bees use for closing gaps. Compositions and methods of this invention can easily be incorporated into such open source bee hive manufacturing.

In essence, as the bee hives age, they incrementally, sporadically or increasingly provide a health benefit to bees from the addition of the above mentioned fungi to offset the increased stressors that occur with bee hives boxes as they get older. The antiviral properties of these fungi, their creation of a wide assortment of complex and simple sugars, the production of p-coumaric acid and other cytochrome p450 activating molecules, the formation of spores of entomopathogenic fungi like *Metarhizium anisopliae* that harm mites but not bees, all work synergistically to counteract the myriad stressors bees suffer from during the lifespan of colonies in hives year to year.

One of numerous examples would be to grow mycelium of, for instance, the polypores *Antrodia cinnomonea, Fomes fomentarius, Inonotus obliquus, Inonotus pini, Fomitopsis officinalis, Fomitopsis pinicola, Fomitiporia robusta, Ganoderma applanatum, Ganoderma australe, Ganoderma atrum, Ganoderma annulare, Ganoderma annularis, Ganoderma brownii, Ganoderma lucidum, Ganoderma resinaceum, Ganoderma tsugae, Lenzites betulina, Phellinus igniarius, Phellinus pini, Phellinus weirii, Piptoporus betulinus, Trametes elegans, Trametes versicolor* and the gilled mushrooms *Schizophyllum commune, Stropharia rugoso-annulata* and *Lentinus ponderosus*. on agricultural waste materials so that the mycelium can be formed into the structural panels used to build bee boxes for honey bees. Additionally, the mite-killing fungus *Metarhizium anisopliae*, can be grown in a preconidial (pre-sporulating) or post conidial (post sporulating) state—or a mixture thereof—and be embedded directly into the constructed panels, no matter what their composition, in combination with the fungi described herein as well as other species this inventor anticipates that could help bees in the Basidiomycetes, Ascomycetes, or the Entomophthorales, Hypocreales, or other fungi attacking mites or phorid flies.

Similarly, chicken coops, bird feeders, plant trellises, etc. may be constructed of cellulosic products impregnated with mycelium and or spores.

Moreover, the aforementioned species and their many relatives contain and secrete toxin degrading enzymes which can help break down insecticides (including neonicitinoids, neonics), fungicides, pesticides, formaldehydes, tannins, dyes, endemic toxins, and a wide array of anthropogenic toxins.

A preferred wood based substrate would be composed of birch panels, boards or sawdust (*Betula* species) and the preferred species would be the birch polypores such as, but not limited to *Fomes fomentarius, Inonotus obliquus, Ganoderma resinaceum* and *Piptoporus betulinus*. If made of conifer woods, then polypores such as *Fomitopsis pinicola, Fomitopsis officinalis, Laetiporus sulphureus, Phellinus igniarius, P. pini, P. linteus* and *P. weirii*; or gilled mushrooms such *Pleurotus ostreatus, Lentinus ponderosus* are ideal candidates. *Trametes versicolor* (=*Coriolus versicolor*) is a polypore mushroom growing on deciduous and conifer woods and is also a preferred species to deploy within the context of this invention. With each of the species listed, they are to be considered in the broadest concept of the species, i.e. 'sensu lato', and close relatives are also anticipated to be useful to helping bees. As such, when describing *Fomitopsis officinalis, Ganoderma applanatum, Ganoderma lucidum, Ganoderma resinaceum, Inonotus obliquus, Trametes versicolor*, or any other mushroom species, this means *Fomitopsis officinalis* sensu lato, *Ganoderma applanatum* sensu lato, *Ganoderma lucidum* sensu lato, *Ganoderma resinaceum* sensu lato, *Inonotus obliquus* sensu lato, *Trametes versicolor* sensu lato and a similar broad description of any other species, each of which means that this is the species concept as described within the broadest taxonomic interpretation, encompassing all historical and modern synonyms, varieties, forms and species that have or will be split from these species since publication. As is known in the art, names change as new species concepts are constructed. The species anticipated to be useful is extremely broad, many of which have been listed in the inventor's previously approved 8 U.S. patents and within the pending patent applications filed to date. Nevertheless, those species not previously listed now become obvious, subsequent to this inventor's discovery.

That the polypore mushrooms *Fomes fomentarius, Inonotus obliquus* and *Ganoderma resinaceum* are active against viruses that harm bees and humans is remarkable, and to the best of the knowledge of this inventor is, medically, unprecedented. Moreover if these cross animal benefits can be obtained from the mycelial extracts of these polypore mushrooms, and indeed many mushrooms, then more than one animal species may benefit from the vast antiviral properties from the mycelia of these species. Hence, bird houses, chicken houses, barns and animal housings of any sort could have the addition of these cultures, their extracts or their spores for immunological and community-protection benefit, preventing disease vectors from escalating and even curing illnesses of its residents within. Potentially homes using mycelium and fungi could protect residents from viruses, bacteria, insects, arthropods, toxins, environmental stressors, disease vectors, and unexpectedly impart pleasant fragrances specific to the fungi deployed.

Extracts useful for the above invention can come as a by-product of those using mycelium for filling forms or molds to create mycelium grown structured materials, such as insulation, shipping materials to replace Styrofoam, building materials, packaging materials, filtration cushions, filtration membranes, fabrics, scaffolding for growing mycelial based computer chips and processors, mycobacterial based nanowires, etc. Additionally, these useful extracts can be harvested by expressing the liquid components from substrates used in all stages of mushroom production as well as from the fungal fermentation methods used for making tempeh, koji, enzymes, antibiotics, plant growth enhancers, and pharmaceuticals. In essence when growing out the mycelium, the mycelially made materials often are dried. In doing so, the extracellular and intracellular metabolites and other liquids must be removed. When growing of mycelium based structured materials, this excess liquid is discarded and not typically highly valued. This invention repurposes this 'waste' liquid product into an unexpected high value-added suite of products that can be rich in antivirals, antimicrobials, enzymes, acids, active ingredients, and other chemicals useful to this invention for helping bees and for many other applications in medicines, chemical engineering, degradation practices, and bioremediation (mycoremediation). Moreover, the now dried myceliated product can be designed so that a latent population of fungal cells survive the drying process, only to be re-activated when the bee hives age, causing the mycelium and its heat-tolerate sclerotia and chlamydospores to survive and re-grow to provide an unusual benefit—as the bee hives age, the impregnated beneficial fungi compete against fungal pathogens, provide nutrients, increase overall bee colony longevity. Beneficial fungi can be selected specifically for heat resistant chlamydospores and sclerotia survivability subsequent to the manufacturing of mycelially grown, structured materials. The repurposed liquid from compressing the mycelium as well as the heat-tolerant mycelium resident within the structured materials can be combined for synergistic benefits to bee health.

Example 31

Honey is collected from bees fed mycelium extracts as above. This medicinal honey helps both bees and people up-regulate pathways for denaturing toxins, via cytochrome P450 pathways. Since honey is a food for more than bees and people, such medicinal honeys are expected to have a wide range of uses. The preservative properties of honey can help keep these medicinally active compounds more stable.

Example 32

α-Amylase, amyloglucosidase, betulinic acid, caffeic acid, protocatechuic acid, trans-cinnamic acid, ferulic acid, gallic acid, ellagic acid, lanosterol, inotodiol, trametenolic acids, hispolons, ergosterols, chrysin, cordycepin, trans-o-coumaric acid, trans-p-coumaric acid, ellagic acid dihydrate, ergosterol, linoleic acids, trans-ferulic acid, gallic acid hydrate, hexanal, hispolon, 4-hydroxybenzoic acid, quercetin hydrate, rutin hydrate, syringic acid, vanillic acid, sulpherinic acid, Dehydrosulphurenic acid, eburicoic acid, 6-chloro-4-phenyl-2H-chromen-2-one, ethyl 6-chloro-2-oxo-4-phenyl-2H-chromen-3-carboxylate, 7-chloro-4-phenyl-2H-chromen-2-one, ethyl 7-chloro-2-oxo-4-phenyl-2H-chromen-3-carboxylate, psilocybin, psilocin and their congeners, isomers, structural analogs and significantly similar compounds may prove useful in the practice of this invention. The compounds are also anticipated to be useful with other animals, including humans.

Example 33

Since protocatechuic acid, vanillic acid, cinnamic acid, caffeic acid and their congeners, isomers, structural analogs and significantly similar compounds are widely distributed and present in many edible plants and with protocatechuic acid being naturally high in bran and grain brown rice, growing bee-benefitting fungal species mentioned herein on a substrate already containing protocatechuic acid, its precursors and analogs, will likely increase the net amount of these bee-benefitting compounds, and is a further embodiment to improve this invention.

Example 33

Extracts of the spores, mycelium and hyphal fragments, or fruitbody tissue of the polypore mushrooms *Fomes fomentarius, Fomitopsis pinicola, Fomitopsis officinalis, Piptoporus betulinus, Ganoderma resinaceum, Ganoderma lucidum, Schizophyllum commune*, and *Inonotus obliquus*, can be aerosolized, or delivered via droplet-clouds, sprayed into hives in combination with a spore-mycelium mixture of *Metarhizium anisopliae*. Such a mixture will reduce viral pathogens, up-regulate detoxification pathways within bees, provide a wide assortment of complex and simple sugars, vitamins to augment immunity and longevity of the hive. Moreover the addition of *Metarhizium anisopliae* spores and mycelium can infect, control and prevent *Varroa* mites and Phorid flies. The endogenous oxalic acid within all these fungi can help control these pathogens. The individual use or combinations of the birch polypores fungi can restrict growth of the *Nosema* microsporidium fungi, and foulbrood bacteria (such as the bacterium *Melissococcus plutonius*) from inflicting harm to the bee colony. Such aerosolized sprays can be delivered using handheld or backpack sprayers. Alternatively, absorbent strips can be deployed infused with the above beneficial agents. Constructed materials used for building the housings of bee boxes can also be soaked and impregnated with these beneficial agents.

I claim:

1. A method for improving bee health comprising adding an extract of a medicinal mushroom mycelium to a feeding supplement for bees to produce a composition for improving bee health and feeding the composition for improving bee health to bees, wherein the composition for improving bee health comprises 1% or less by volume of the extract, and wherein the medicinal mushroom mycelium is selected from the group consisting of *Inonotus obliquus, Ganoderma resinaceum, Fomitopsis pinicola, Fomes fomentarius, Schizophyllum commune, Trametes versicolor, Fomitopsis officinalis, Ganoderma applanatum, Ganoderma lucidum* and combinations thereof.

2. The method of claim 1 wherein the feeding supplement for bees comprises a product selected from the group consisting of water, sugars, sugar syrup, high fructose corn syrup water, bee candy, nectar, pollen, pollen patties, grease patties, propolis, bees wax, bee sprays, bee feed, protein supplements and combinations thereof.

3. The method of claim 1 wherein the medicinal mushroom mycelium is cultivated on a substrate selected from the group consisting of solid substrates and liquid substrates.

4. The method of claim 1 wherein the extract of a medicinal mushroom mycelium is selected from the group consisting of an aqueous extract of medicinal mushroom mycelium, an aqueous ethanolic extract of medicinal mushroom mycelium, precipitate from an aqueous extract of medicinal mushroom mycelium precipitated by addition of ethanol, supernatant remaining after the precipitate from an aqueous extract of medicinal mushroom mycelium precipitated by addition of ethanol is removed, precipitate from an aqueous ethanolic extract of medicinal mushroom mycelium allowed to sit, concentrate from aqueous ethanolic extract of medicinal mushroom mycelium which has had a portion of the solvent removed, supernatant from aqueous ethanolic extract which has had a portion of solvent removed, an extract of medicinal mushroom mycelium from which solvent has been removed, non-aqueous and non-ethanolic solvent extract of medicinal mushroom mycelium, subcritical extract and supercritical extract of medicinal mushroom mycelium and microwave-assisted extract of medicinal mushroom mycelium.

5. The method of claim 1 wherein the composition for improving bee health additionally comprises a miticide selected from the group consisting of synthetic miticides, natural miticides and combinations thereof, and wherein the natural miticides are selected from the group consisting of Neem extracts, oxalic acid, formic acid, lactic acid, spores of entomopathogenic fungi pathogenic to mites, hyphaeof entomopathogenic fungi pathogenic to mites, preconidial mycelium of entomopathogenic fungi pathogenic to mites, extracts of preconidial mycelium of entomopathogenic fungi pathogenic to mites and combinations thereof.

6. The method of claim 1 wherein the composition for improving bee health improves the health of bees by increasing longevity by more than 3%.

7. The method of claim 1 wherein the composition for improving bee health improves the health of bees by reducing viral load by more than 15%.

8. The method of claim 1 wherein the composition for improving bee health improves the health of bees by increasing longevity and reducing viral load by an LV index of more than 45.

9. A method for improving bee health comprising applying a composition for improving bee health to an object selected from the group consisting of beehives, beehive components, bees wax, bees and combinations thereof, wherein the composition for improving bee health comprises 1% or less by volume of an extract of a medicinal mushroom mycelium and wherein the medicinal mushroom mycelium is selected from the group consisting of *Inonotus obliquus, Ganoderma resinaceum, Fomitopsis pinicola, Fomes fomentarius, Schizophyllum commune, Trametes versicolor, Fomitopsis officinalis, Ganoderma applanatum, Ganoderma lucidum* and combinations thereof.

10. The method of claim 7 wherein the composition for improving bee health additionally comprises a miticide selected from the group consisting of synthetic miticides, natural miticides and combinations thereof, and wherein the natural miticides are selected from the group consisting of Neem extracts, oxalic acid, formic acid, lactic acid, and combinations thereof.

11. The method of claim 7 wherein the medicinal mushroom mycelium is cultivated on a substrate selected from the group consisting of solid substrates and liquid substrates.

12. The method of claim 7 wherein the extract of a medicinal mushroom mycelium is selected from the group consisting of an aqueous extract of medicinal mushroom mycelium, an aqueous ethanolic extract of medicinal mushroom mycelium, precipitate from an aqueous extract of medicinal mushroom mycelium precipitated by addition of ethanol, supernatant remaining after the precipitate from an aqueous extract of medicinal mushroom mycelium precipitated by addition of ethanol is removed, precipitate from an aqueous ethanolic extract of medicinal mushroom mycelium allowed to sit, concentrate from aqueous ethanolic extract of medicinal mushroom mycelium which has had a portion of the solvent removed, supernatant from aqueous ethanolic extract which has had a portion of solvent removed, an extract of medicinal mushroom mycelium from which solvent has been removed, non-aqueous and non-ethanolic solvent extract of medicinal mushroom mycelium, subcritical extract and supercritical extract of medicinal mushroom mycelium and microwave-assisted extract of medicinal mushroom mycelium.

13. The method of claim 1 further comprising at least one extract of a medicinal mushroom mycelium selected from the group consisting of *Antrodia cinnomonea, Ganoderma atrum, Ganoderma brownii, Ganoderma curtisii, Ganoderma lucidum, Ganoderma lingzhi, Ganoderma oregonense, Ganoderma tsugae, Fomitopsis officinalis* (*Laricifomes officinalis*), *Fomitiporia robusta, Heterobasidion annosum, Inonotus hispidus, Inonotus andersonii, Inonotus dryadeus, Laetiporus cincinnatus, Laetiporus sulphureus, Laetiporus conifericola, Lenzites betulina, Phellinus igni-*

*arius, Phellinus linteus, Phellinus pini, Piptoporus betulinus, Polyporus elegans, Stereum complicatum, Stereum hirsutum, Stereum ostrea, Trametes elegans, Trametes gibbosa, Trametes hirsuta, Trametes villosa, Trametes cingulata, Trametes ochracea, Trametes pubescens, Trametes ectypa, Trametes aesculi, Wolfiporia cocos, Agaricus augustus, Agaricus blazei, Agaricus bonardii, Agaricus brasiliensis, Agaricus campestris, Agaricus lilaceps, Agaricus subrufescens, Agaricus sylvicola, Agrocybe pediades, Agrocybe aegerita, Agrocybe arvalis, Agrocybe praecox, Clitocybe odora, Conocybe cyanopus, Conocybe lacteus, Conocybe rickenii, Conocybe smithii, Conocybe tenera, Coprinopsis nivea, Coprinopsis lagopus, Coprinus comatus, Coprinus micaceus, Gymnopus hydrophilus, Gymnopus peronatus, Hypholoma aurantiaca (Leratiomyces ceres), Hypholoma capnoides, Hypholoma sublateritium, Hypsizygus marmoreus, Hypsizygus tessulatus, Hypsizygus ulmarius, Lentinus ponderosus, Lepiota procera (Macrolepiota procera), Lepiota rachodes (Chlorophyllum rachodes), Lepista nuda, Mycena alcalina, Mycena pura, Mycena aurantiadisca, Panellus serotinus, Panaeolus foenisecii, Panaeolus subbalteatus, Pleurotus columbinus, Pleurotus ostreatus, Pleurotus cystidiosus, Pleurotus pulmonarius, Pleurotus sapidus, Pleurotus tuberregium, Panellus stipticus, Panellus serotinus, Pluteus cervinus, Psathyrella aquatica, Psathyrella condolleana, Psathyrella hydrophila, Psilocybe allenii, Psilocybe azurescens, Psilocybe caerulescens, Psilocybe coprophila, Psilocybe cubensis, Psilocybe cyanescens, Psilocybe ovoideocystidiata, Psilocybe stuntzii, Psilocybe subaeruginosa, Stropharia aeruginosa, Stropharia cyanea, Stropharia rugoso-annulata, Stropharia semiglobata, Stropharia semigloboides, Stropharia squamosa, Stropharia thrausta, Stropharia umbonotescens, Termitomyces robusta, Volvaria bombycina, Volvariella volvacea* and combinations thereof and wherein the composition comprises a total amount of 1% or less by volume of mushroom mycelium extract.

14. A method for improving bee health comprising adding an extract of a medicinal mushroom mycelium to a feeding supplement for bees to produce a composition for improving bee health and feeding the composition for improving bee health to bees, wherein the composition comprises 10% or less by volume of the extract of a medicinal mushroom mycelium and wherein the medicinal mushroom mycelium is selected from the group consisting of *Fomes fomentarius, Trametes versicolor*, and a combination thereof.

* * * * *